(12) United States Patent
Alani et al.

(10) Patent No.: US 11,427,641 B2
(45) Date of Patent: Aug. 30, 2022

(54) EXTENDED LOCAL RELEASE OF ANTI-CSFR1 ANTIBODIES

(71) Applicant: AmMax Bio, Inc., Redwood City, CA (US)

(72) Inventors: Laman Alani, Menlo Park, CA (US); Chung-Chiang Hsu, Los Altos Hills, CA (US); Kirk William Johnson, Moraga, CA (US)

(73) Assignee: AmMax Bio, Inc., Redwood City, CA (US)

( * ) Notice: Subject to any disclaimer, the term of this patent is extended or adjusted under 35 U.S.C. 154(b) by 0 days.

(21) Appl. No.: 17/571,398

(22) Filed: Jan. 7, 2022

(65) Prior Publication Data
US 2022/0204632 A1    Jun. 30, 2022

Related U.S. Application Data

(63) Continuation of application No. PCT/US2021/065222, filed on Dec. 27, 2021.

(60) Provisional application No. 63/187,251, filed on May 11, 2021, provisional application No. 63/186,639, filed on May 10, 2021, provisional application No. 63/132,433, filed on Dec. 30, 2020.

(51) Int. Cl.
| | | |
|---|---|---|
| *C07K 16/28* | (2006.01) | |
| *A61K 9/08* | (2006.01) | |
| *A61K 9/00* | (2006.01) | |
| *A61K 47/36* | (2006.01) | |

(52) U.S. Cl.
CPC ........ *C07K 16/2866* (2013.01); *A61K 9/0019* (2013.01); *A61K 9/08* (2013.01); *A61K 47/36* (2013.01); *C07K 2317/24* (2013.01); *C07K 2317/51* (2013.01); *C07K 2317/515* (2013.01)

(58) Field of Classification Search
CPC ... C07K 16/2866; A61K 9/0019; A61K 47/36
See application file for complete search history.

(56) References Cited

U.S. PATENT DOCUMENTS

| | | | | |
|---|---|---|---|---|
| 8,529,897 | B2 * | 9/2013 | Washburn | ................. A61P 1/00 424/134.1 |
| 2014/0328764 | A1 * | 11/2014 | Tang | .................... G01N 33/582 435/23 |

FOREIGN PATENT DOCUMENTS

WO    2017175200 A1    10/2017

OTHER PUBLICATIONS

International Search Report and Written Opinion of the International Searching Authority for International Application No. PCT/US21/65222, International Filing Date Dec. 27, 2021, dated May 4, 2022, (12 pages).
Mach et al. "Electrostatic interactions of monoclonal antibodies with subcutaneous tissue" Ther Deliv, Jun. 2011, vol. 2, No. 6, pp. 1-10, especially, Abstract; p. 5, col. 1, para 1; p. 6,col. 1, para 1; p. 6, col. 2, para 2; Fig. 5; Fig. o/; Fig. 8; Fig. 7 legend, (11 pages).
Tian et al. "Hyaluronic acid hydrogel as Nogo-66 receptor antibody delivery system for the repairing of injured rat brain: in vitro" Journal of Controlled Release. 2005, vol. 102, No. 1, pp. 13-22, whole document, (10 pages).

* cited by examiner

*Primary Examiner* — Elly-Gerald Stoica
(74) *Attorney, Agent, or Firm* — Sheppard Mullin Richter & Hampton LLP

(57) ABSTRACT

The present disclosure provides compositions and methods for extended release of certain types of antibodies in vivo. It was discovered that such antibodies are able to initiate reversible gelation of hyaluronic acid (HA) by creating a depot that dissociates over time to release the antibody without any impact on its physical and chemical properties as well as its biological activity. As certain tissues and organs, such as eyes, joints and skins, contain HA, local injection of the antibodies to these tissues or organs will result in embedding of the antibody in gel formed from the HA, which becomes a repository of slow-released antibodies. In addition, slow-released formulations can be prepared with antibodies mixed with HA, optionally with other polymers.

5 Claims, 3 Drawing Sheets
Specification includes a Sequence Listing.

SEQUENCE LISTING

```
<160> NUMBER OF SEQ ID NOS: 16

<210> SEQ ID NO 1
<211> LENGTH: 446
<212> TYPE: PRT
<213> ORGANISM: Artificial Sequence
<220> FEATURE:
<223> OTHER INFORMATION: Synthetic

<400> SEQUENCE: 1
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Asp | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Val | Ile | Trp | Thr | Asp | Gly | Gly | Thr | Asn | Tyr | Ala | Gln | Lys | Leu | Gln |
| | 50 | | | | | 55 | | | | | 60 | | | | |
| Gly | Arg | Val | Thr | Met | Thr | Thr | Asp | Thr | Ser | Thr | Ser | Thr | Ala | Tyr | Met |
| 65 | | | | | 70 | | | | | 75 | | | | | 80 |
| Glu | Leu | Arg | Ser | Leu | Arg | Ser | Asp | Asp | Thr | Ala | Val | Tyr | Tyr | Cys | Ala |
| | | | | 85 | | | | | 90 | | | | | 95 | |
| Arg | Asp | Gln | Arg | Leu | Tyr | Phe | Asp | Val | Trp | Gly | Gln | Gly | Thr | Thr | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| | | 130 | | | | | 135 | | | | | 140 | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | | 275 | | | | | 280 | | | | | 285 | | |
| Lys | Pro | Arg | Glu | Glu | Gln | Tyr | Asn | Ser | Thr | Tyr | Arg | Val | Val | Ser | Val |
| | | 290 | | | | | 295 | | | | | 300 | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 2
<211> LENGTH: 213
<212> TYPE: PRT
<213> ORGANISM: Artificial Sequence
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 449
```

```
<212> TYPE: PRT
<213> ORGANISM: Artificial Sequence
<220> FEATURE:
<223> OTHER INFORMATION: Synthetic

<400> SEQUENCE: 3
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
        435                 440                 445

Lys

<210> SEQ ID NO 4
<211> LENGTH: 218
<212> TYPE: PRT
<213> ORGANISM: Artificial Sequence
<220> FEATURE:
<223> OTHER INFORMATION: Synthetic

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 5
<211> LENGTH: 450
<212> TYPE: PRT
<213> ORGANISM: Artificial Sequence
<220> FEATURE:
<223> OTHER INFORMATION: Synthetic

<400> SEQUENCE: 5

Gln Asp Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Glu Val Asp Tyr Gly Met Asp Val Trp Gly Gln
            100                 105                 110

Gly Thr Thr Val Thr Val Ala Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

Gly Lys
    450

<210> SEQ ID NO 6
<211> LENGTH: 214
<212> TYPE: PRT
<213> ORGANISM: Artificial Sequence
<220> FEATURE:
<223> OTHER INFORMATION: Synthetic

<400> SEQUENCE: 6

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 446
<212> TYPE: PRT
<213> ORGANISM: Artificial Sequence
<220> FEATURE:
<223> OTHER INFORMATION: Synthetic

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

```
Gln Gly Arg Val Thr Met Thr Thr Asp Thr Ser Thr Ala Tyr
 65              70                  75                  80

Met Glu Leu Arg Ser Leu Arg Ser Asp Thr Ala Val Tyr Tyr Cys
             85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 8
<211> LENGTH: 220
<212> TYPE: PRT
<213> ORGANISM: Artificial Sequence
<220> FEATURE:
<223> OTHER INFORMATION: Synthetic
```

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 9
<211> LENGTH: 453
<212> TYPE: PRT
<213> ORGANISM: Artificial Sequence
<220> FEATURE:
<223> OTHER INFORMATION: Synthetic

<400> SEQUENCE: 9

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Asp Asp Asp Lys Tyr Tyr Asn Pro Ser
    50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Gln Gly Thr Met Val Thr Val Ser Ser Ala Ser
        115                 120                 125

```
Thr Lys Gly Pro Ser Val Phe Pro Leu Ala Pro Cys Ser Arg Ser Thr
    130                 135                 140
Ser Glu Ser Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Lys Thr Tyr Thr
        195                 200                 205
Cys Asn Val Asp His Lys Pro Ser Asn Thr Lys Val Asp Lys Arg Val
210                 215                 220
Glu Ser Lys Tyr Gly Pro Pro Cys Pro Pro Cys Pro Ala Pro Glu Phe
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser Gln Glu Asp Pro Glu Val Gln Phe Asn Trp Tyr Val Asp Gly Val
        275                 280                 285
Glu Val His Asn Ala Lys Thr Lys Pro Arg Glu Glu Gln Phe Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Gly Leu Pro Ser
                325                 330                 335
Ser Ile Glu Lys Thr Ile Ser Lys Ala Lys Gly Gln Pro Arg Glu Pro
            340                 345                 350
Gln Val Tyr Thr Leu Pro Pro Ser Gln Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Arg Leu
                405                 410                 415
Thr Val Asp Lys Ser Arg Trp Gln Glu Gly Asn Val Phe Ser Cys Ser
            420                 425                 430
Val Met His Glu Ala Leu His Asn His Tyr Thr Gln Lys Ser Leu Ser
        435                 440                 445
Leu Ser Leu Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15
Asp Arg Val Thr Ile Thr Cys Leu Ala Ser Glu Asp Ile Tyr Asp Asn
            20                  25                  30
```

```
Leu Ala Trp Tyr Gln Gln Lys Pro Gly Lys Ala Pro Lys Leu Leu Ile
         35                  40                  45

Tyr Tyr Ala Ser Ser Leu Gln Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Asp Ser Glu Tyr Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 448
<212> TYPE: PRT
<213> ORGANISM: Artificial Sequence
<220> FEATURE:
<223> OTHER INFORMATION: Synthetic

<400> SEQUENCE: 11

Gln Val Gln Leu Gln Glu Ser Gly Pro Gly Leu Val Lys Pro Ser Gln
 1               5                  10                  15

Thr Leu Ser Leu Thr Cys Thr Val Ser Asp Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Tyr Asn Pro Ser Leu
 50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Synthetic

<400> SEQUENCE: 12

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Thr Asp Gln Ala Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
     210

<210> SEQ ID NO 13
<211> LENGTH: 447
<212> TYPE: PRT
<213> ORGANISM: Artificial Sequence
<220> FEATURE:
<223> OTHER INFORMATION: Synthetic

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
             20                  25                  30

Tyr Ala Trp Asn Trp Ile Arg Gln Phe Pro Gly Asn Lys Leu Glu Trp
         35                  40                  45

Met Gly Tyr Ile Ser Tyr Ser Gly Ser Thr Ser Tyr Asn Pro Ser Leu
     50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Phe Asp Tyr Ala His Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445

<210> SEQ ID NO 14
<211> LENGTH: 214
<212> TYPE: PRT
<213> ORGANISM: Artificial Sequence
<220> FEATURE:
<223> OTHER INFORMATION: Synthetic

<400> SEQUENCE: 14

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Thr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

```
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 15
<211> LENGTH: 447
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Thr Trp Val Arg Gln Ala Pro Gly Lys Gly Leu Glu Trp Val
        35                  40                  45

Ser Tyr Ile Ser Ser Arg Ser Ser Thr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Pro Leu Leu Ala Gly Ala Thr Phe Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300
```

```
Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 16
<211> LENGTH: 215
<212> TYPE: PRT
<213> ORGANISM: Artificial Sequence
<220> FEATURE:
<223> OTHER INFORMATION: Synthetic

<400> SEQUENCE: 16

Glu Phe Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

EXTENDED LOCAL RELEASE OF ANTI-CSFR1 ANTIBODIES

CROSS REFERENCE TO RELATED APPLICATIONS

This application is a continuation of International Patent Application PCT/US2021/065222, filed Dec. 27, 2021, which claims the benefit under 35 U.S.C. § 119(e) of U.S. Provisional Application Ser. No. 63/132,433, filed Dec. 30, 2020, which claims the benefit under 35 U.S.C. § 119(e) of U.S. Provisional Application Ser. No. 63/186,639, filed May 10, 2021, and U.S. Provisional Application Ser. No. 63/187,251, filed May 11, 2021, the content of each of which is incorporated by reference in its entirety into the present disclosure.

SEQUENCE LISTING

The instant application contains a Sequence Listing which has been submitted in ASCII format via EFS-Web and is hereby incorporated by reference in its entirety. Said ASCII copy, created on Jan. 6, 2022, is named 72GZ_325889_US_ST25.txt and is 49,152 bytes in size.

BACKGROUND

Certain localized diseases, in particular chronic diseases, can benefit from localized delivery of a therapeutic agent as it can minimize potential side effects to other tissues while concentrating the therapeutic effect locally. One of the major localized deliveries is by local injection, such as intraarticular injection. As such injections need to be carried out by trained medical professionals, there is a strong need to develop formulations that can deliver a large amount of the therapeutic agent through an extended period of time.

Tenosynovial giant cell tumor (TGCT) is an example localized disease, which can also diffuse to nearby tissues. TGCT is a neoplasm derived from the synovium that causes recruitment of immune cells, specifically macrophages, leading to formation of a mass. These tumors are often classified by their growth pattern (localized or diffuse) and site (intra- or extra-articular).

Localized TGCT is characterized by a discrete nodule. While any location is possible, localized forms mainly involve the digits joints and wrist (85% of cases). Foot and ankle, knee, hip or other joint locations are rarer. Diffuse forms mainly involve the large joints: knee, hip, ankle and elbow. Localized forms are systematically benign; diffuse forms are more aggressive and destructive and may exceptionally include a malignant component.

Current treatment options for TGCT are limited, including surgery and radiotherapy. Surgery is often the treatment of choice for patients with TGCT. Localized TGCT is managed by marginal excision. Recurrences occur in 8-20% of patients and are managed by re-excision. Diffuse TGCT/PVNS tends to recur more often (33-50%) and has a much more aggressive clinical course. Patients are often symptomatic and require multiple surgical procedures during their lifetime. In some cases, the joint may need to be replaced.

A potential therapy for TGCT targets a cytokine called colony stimulating factor 1 (CSF1) or its receptor, colony stimulating factor 1 receptor (CSF1R).

CSF1R-mediated signaling is crucial for the differentiation and survival of the mononuclear phagocyte system. Intratumoral presence of CSF1R-positive macrophages correlate with poor survival in various tumor types, targeting CSF1R signaling in tumor-promoting tumor-associated macrophage represents an attractive strategy to eliminate or repolarize these cells.

Several anti-CSF1 and anti-CSF1R antibodies are in clinical development, for treating various solid tumors. Examples include emactuzumab (anti-CSF1R, SynOx and Roche), cabiralizumab (anti-CSF1R, Five Prime and BMS), lacnotuzumab (anti-CSF1, Novartis and Xoma), PD-0360324 (anti-CSF1, Pfizer), axatilimab (anti-CSF1R, Syndax and UCB Biopharma), and IMC-CS4 (anti-CSF1R, Eli Lilly and Imclone). Safety of this class of compounds present challenges to realize the value of the therapeutic effect such as elevated liver enzyme and edema. The development of extended release formulation and methodology for the anti-CSF1 and anti-CSF1R antibodies can be useful for the treatment of many indications.

SUMMARY

The present disclosure reports the surprising reversible interaction between an antibody, e.g., AM001 and Emactuzumab, with hyaluronic acid (HA), to produce a mass that dissociates slowly. The slow erosion and release produce a prolonged biological effect (acting as a depo) without impact on the antibody's biological activity, or its chemical or physical integrity. Accordingly, the present disclosure provides compositions that includes an antibody and HA suitable for extended release of the antibody, and methods of delivering an antibody to a tissue that contains HA.

One embodiment of the present disclosure provides a method for providing extended release of an antibody in a mammalian subject in need thereof, comprising injection of an aqueous solution comprising the antibody to or near a tissue (or joint) in the mammalian subject, wherein the tissue contains hyaluronic acid (HA), and the solution has a pH that is at least 0.5 below the isoelectric point (pI) of the antibody.

In some embodiments, the solution comprises at least 15 mg/mL of the antibody, preferably at least 25 mg/mL, 30 mg/mL, 50 mg/mL, 60 mg/mL, 80 mg/mL, or 100 mg/mL of the antibody.

In some embodiments, the solution does not include more than 100 mM of an alkaline salt or a salt of an amino acid, preferably does not include more than 50 mM, 20 mM or 10 mM of the salt. In some embodiments, the salt is NaCl or a salt of arginine.

In some embodiments, the solution has a pH that is 0.7-1.5 below the isoelectric point (pI) of the antibody.

In some embodiments, the antibody is AM001, and the solution has a pH between 4.5 and 5.5, wherein AM001 comprises a heavy chain comprising the amino acid sequence of SEQ ID NO:7 and a light chain comprising the amino acid sequence of SEQ ID NO:8. In some embodiments, the solution has a pH of 5 to 5.3.

In some embodiments, the antibody is Emactuzumab, and the solution has a pH between 5.5 and 6.5. In some embodiments, the solution has a pH of 6.2 to 6.4.

In some embodiments, the tissue is a joint. In some embodiments, the joint is an elbow, a wrist, an ankle or a knee. In some embodiments, the injection is intraarticular injection.

In some embodiments, the tissue is a dermal tissue. In some embodiments, the injection is subcutaneous injection.

In some embodiments, the tissue is an ocular tissue. In some embodiments, the injection is intravitreal injection.

In some embodiments, the solution further comprises HA. In some embodiments, the solution comprises 0.1 to 1.5 w/v % HA, preferably 0.2 to 0.5 w/v % HA.

In some embodiments, the injection is once every 2 weeks, 3 weeks, 4 weeks, 2 months, 3 months, 4 months, 6 months, or longer.

Also provided, in one embodiment, is a composition comprising at least 15 mg/mL of an antibody, 0.1 to 1.5 w/v % hyaluronic acid (HA), and water, wherein the composition has a pH that is at least 0.5 below the isoelectric point (pI) of the antibody. In some embodiments, the antibody is embedded in a gel comprising the HA.

In some embodiments, the composition comprises at least 15 mg/mL of the antibody, preferably at least 25 mg/mL, 30 mg/mL, 50 mg/mL, 60 mg/mL, 80 mg/mL, or 100 mg/mL of the antibody.

In some embodiments, the composition does not include more than 100 mM of an alkaline salt or a salt of an amino acid, preferably does not include more than 50 mM, 20 mM or 10 mM of the salt. In some embodiments, the salt is NaCl or a salt of arginine.

In some embodiments, the composition has a pH that is 0.7-1.5 below the isoelectric point (pI) of the antibody. In some embodiments, the antibody is AM001, and the composition has a pH between 4.5 and 5.5, wherein AM001 comprises a heavy chain comprising the amino acid sequence of SEQ ID NO:7 and a light chain comprising the amino acid sequence of SEQ ID NO:8. In some embodiments, the composition has a pH of 5 to 5.3.

In some embodiments, the antibody is Emactuzumab, and the composition has a pH between 5.5 and 6.5. In some embodiments, the composition has a pH of 6.2 to 6.4.

In some embodiments, the composition comprises 0.1 to 1.2 w/v % HA, preferably 0.1 to 1.0 w/v % HA, 0.2 to 0.8 w/v % HA, or 0.2 to 0.5 w/v % HA.

DETAILED DESCRIPTION

I. Definitions

Figure 1:
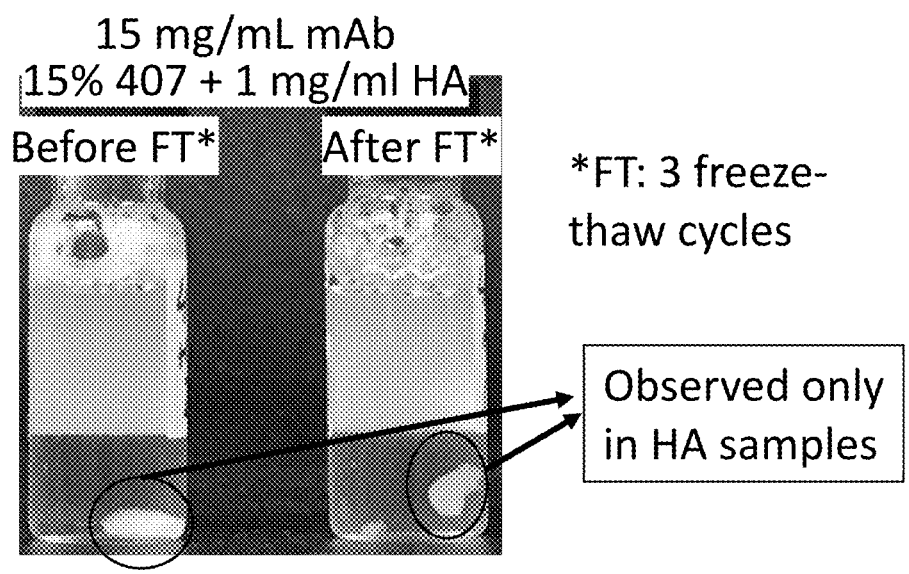
FIG. 1 shows that addition of hyaluronic acid (HA) and poloxamer 407 (407) to a solution of AM001 formed a small lump of wax-like material. The wax-like material was observed both before and after three freeze-thaw cycles (FT), but not in samples in which only 407 was added.

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

The term "administration" refers to introducing an agent into a patient. An effective amount can be administered, which can be determined by the treating physician or the like. The related terms and phrases administering" and "administration of", when used in connection with a compound or tablet (and grammatical equivalents) refer both to direct administration, which may be administration to a patient by a medical professional or by self-administration by the patient.

"Therapeutically effective amount" or "effective amount" refers to an amount of a drug or an agent that when administered locally via a pharmaceutical composition described herein to a patient suffering from a condition, will have an intended therapeutic effect, e.g., alleviation, amelioration, palliation or elimination of one or more symptoms of the condition in the patient. The full therapeutic effect does not necessarily occur immediately and may occur only after a therapeutically effective amount is being delivered continuously for a period of time. For slow release or controlled release formulation, "therapeutically effective amount" or "effective amount" may refer to the total amount that is effective over a period of time, which is slowly released from the delivery vehicle to the disease site at an ascertainable and controllable release rate that constantly provides an effective amount of the drug to the disease site. In some embodiments, "therapeutically effective amount" or "effective amount" refers to an amount released to the disease site at a given period of time, e.g., per day.

The term "near," when referring to a tissue targeted for administration, means the intended target tissue and surrounding area. In some embodiments, the proximity is within 5 cm, 4 cm, 3 cm, 2 cm, 1.5 cm, 1 cm, 0.8 cm, 0.6 cm, 0.5 cm, 0.4 cm, 0.3 cm, 0.2 cm or 0.1 cm from the tissue.

The term "biodegradable," as used herein, means a polymer that dissolves or degrades within a period that is acceptable in the desired application, less than about five years and most preferably less than about one year, after exposure to a biological environment. For example, a polymer may be biodegradable in a physiological solution of pH 5-8 at a temperature of between about 25° C. and 38° C.

The term "pharmaceutically acceptable" refers to generally safe and non-toxic for human administration.

"Treatment", "treating", and "treat" are defined as acting upon a disease, disorder, or condition with an agent to reduce or ameliorate the harmful or any other undesired effects of the disease, disorder, or condition and/or its symptoms.

Unless otherwise specified, the terms "drug," "active ingredient," "active pharmaceutical ingredient," "therapeutic agent" and "API" are used synonymously to refer to the component in the composition that has a desired therapeutic effect.

"Antibody" means a human or non-human antibody, including humanized antibodies, and may be polyclonal or monoclonal, and/or chimeric antibodies. The term "antibody" includes antibody fragments capable of binding to antigen and may be selected from Fab, an Fv, an scFv, Fab' and Fab". The antibody may be of any isotype. The antibody can be wild-type or can include one or more mutations. For example, the mutation may be a conservative substitution of a cysteine residue. An "anti-CSF1R antibody" has the corresponding meaning with respect to an antibody to the CSF1R receptor.

Colony stimulating factor 1 (CSF-1), also known as macrophage colony stimulating factor (M-CSF), is a cytokine produced by a variety of cells, including macrophages, endothelial cells and fibroblasts. CSF-1 is composed of two "monomer" polypeptides, which form a biologically active dimeric CSF-1 protein. CSF-1 exists in at least three mature forms due to alternative RNA splicing (see, e.g., Cerretti et al. Molecular Immunology, 25:761 (1988)). The three forms of CSF-1 are translated from precursors, which encode polypeptide monomers of 256 to 554 amino acids, having a 32 amino acid signal sequence at the amino terminal and a putative transmembrane region of approximately 23 amino acids near the carboxyl terminal. The precursor peptides are subsequently processed by amino terminal and carboxyl terminal proteolytic cleavages to release mature CSF-1. Residues 1-149 of all three mature forms of CSF-1 are identical and are believed to contain sequences essential for biological activity of CSF-1. CSF-1 monomers are dimerized in vivo via disulfide-linkage and are glycosylated. CSF-1 belongs to a group of biological agonists that promote the production of blood cells. Specifically, it acts as a growth and differentiation factor for bone marrow progenitor cells of the mononuclear phagocyte lineage.

Colony stimulating factor 1 receptor (referred to herein as CSF1R; also referred to as FMS, FIM2, C-FMS, or CD115) is a single-pass transmembrane receptor with an N-terminal extracellular domain (ECD) and a C-terminal intracellular domain with tyrosine kinase activity. CSF1R belongs to the type III protein tyrosine kinase receptor family, and binding of CSF1 or the interleukin 34 ligand induces homodimerization of the receptor and subsequent activation of receptor signaling. CSF1R-mediated signaling is crucial for the differentiation and survival of the mononuclear phagocyte system and macrophages in particular.

"Thermogel" refers to a composition, which undergoes a phase transition from a liquid phase to gel phase when the temperature is raised above or reduced below a critical value, which is referred to as "transition temperature" or "gelation temperature." Preferably the thermogel is thermoreversible. The term "liquid phase" or "liquid state" refers to a liquid or flowable form, such as a state having a viscosity of less than 2000 Pascal-seconds. The term "gel phase" or "gel state" refers to a gel or relatively solid form, such as a state having a viscosity of greater than 10,000 Pascal-seconds. In some embodiments, the phase transition from a liquid to a gel and vice versa occurs in less than 10 minutes, or in less than 5 minutes or in less than 2 minutes.

"Gel" refers to a semi-solid phase. For example, when the temperature of a thermogel is raised to or above the gelation temperature of the thermogel, the thermogel becomes a gel while it behaves as liquid at temp below the gelation temperature.

"Aqueous solvent" refers to water or a water-based solution, e.g. an aqueous salt solution, such as a saline solution, phosphate buffered saline (PBS), and other aqueous solutions suitable for preparing an injectable pharmaceutical composition. An aqueous salt solution may contain one or more biocompatible salts selected from sodium chloride (NaCl), potassium chloride (KCl), sodium sulfate ($Na_2SO_4$), sodium bisulfate ($NaHSO_4$), sodium phosphate ($Na_3PO_4$), monosodium phosphate ($NaH_2PO_4$), disodium phosphate ($Na_2HPO_4$), potassium phosphate ($K_3PO_4$), monopotassium phosphate ($KH_2PO_4$), dipotassium phosphate ($K_2HPO_4$), various soluble calcium and magnesium salts, such as calcium chloride ($CaCl_2$), magnesium chloride ($MgCl_2$) and other salts formed by a combination of a cation selected from the group consisting of sodium, potassium, calcium, magnesium, ammonium, and tetraalkylammonium, with an anion selected from the group consisting of chloride, bromide, tartrate, mesylate, acetate, maleate, and oxalate and other biocompatible, water soluble salts including those described in P. Heinrich Stahl, Camille G. Wermuth (Eds.), Handbook of Pharmaceutical Salts Properties, Selection, and Use; 2002.

II. Gelation of Administered Antibodies In Situ

In a surprising discovery of the present disclosure, when hyaluronic acid (HA) was added to a solution of antibody AM001, gelation of the HA and the antibody ensued. The gel retained even after dilutions, but was nevertheless reversible. More surprisingly, such gelation was observed with endogenous HA as well. When a solution of AM001 was injected into the joints, it formed gels with endogenous HA present in the joints. By contrast, antibody pembrolizumab did not trigger gelation of HA in vitro or in vivo at the conditions tested.

Moreover, the gelation effect on HA is not limited to joints. In Example 3, when AM001 was administered subcutaneously, a rapid onset of activity with complete plateau ensued (for at least three weeks), suggesting that the HA in the dermal tissue formed a depot with the antibody, extending its release in the body.

These discoveries are unexpected for a few reasons. First, to the best knowledge of the inventors, there has been no report that HA gelation is activated by a protein, much less an antibody. Second, such gelation is reversible, which allows slow release of the antibody into the nearby tissues, and brings about minimized impact to the natural function of the HA. Third, the ability to activate HA gelation only occurs under certain conditions.

Additional experiments shown in Examples 4-8 demonstrate that the gelation between the antibody and HA is due to ion-pairing of positively charged antibodies with HA. Such ion-pairing can only happen when the antibody is present at a pH lower than its isoelectric point (pI) and preferably in the absence of excipient having high ionic strength, such as NaCl or Arg*HCl.

In accordance with one embodiment of the disclosure, therefore, provided is a method for providing extended release of an antibody in a mammalian subject in need thereof. In some embodiments, the method entails local administration of a composition comprising the antibody to, or near, a tissue in the mammalian subject, wherein the tissue contains hyaluronic acid (HA). In some embodiments, the antibody is able to activate gelation of the HA in the tissue.

Hyaluronic acid (HA, or hyaluronan) is an anionic, non-sulfated glycosaminoglycan distributed widely throughout connective, epithelial, and neural tissues. Human synovial HA averages about 7 million Da per molecule, or about 20,000 disaccharide monomers. As one of the chief components of the extracellular matrix, it contributes to cell proliferation and migration. The average 70 kg (154 lb) person has roughly 15 grams of hyaluronan in the body, one-third of which is turned over (i.e., degraded and synthesized) per day.

Hyaluronic acid is a major component of the synovial fluid, and intravitreal fluid and can increase the viscosity of the fluid. Along with lubricin, it is one of the fluid's main lubricating components. Hyaluronic acid is an important component of articular cartilage, where it is present as a coat around each cell (chondrocyte). When aggrecan monomers bind to hyaluronan in the presence of HAPLN1 (Hyaluronan And Proteoglycan Link Protein 1), large, highly negatively charged aggregates form. These aggregates imbibe water and are responsible for the resilience of cartilage.

Hyaluronic acid is also a major component of skin, where it is involved in repairing tissue. When skin is exposed to excessive UVB rays, it becomes inflamed and the cells in the dermis stop producing as much hyaluronan, and increase the rate of its degradation. It is found in a thick layer of the skin called the dermis, which is essential in maintaining skin structure, and functions as a protective barrier between the environment and the body. Also, hyaluronic acid helps maintain the moisture of the skin because it binds water.

In one embodiment, the tissue that contains HA is a connective tissue. In one embodiment, the tissue that contains HA is a skin tissue. In one embodiment, the tissue that contains HA is an ocular tissue which is close to or contains intravitreal fluid. In one embodiment, the tissue that contains HA is a joint, such as elbow, wrist, ankle and knee.

"Extended release," "controlled release", "sustained release", or "slow release" and similar terms are used to denote a mode of active agent delivery that occurs when the active agent is released from the delivery vehicle or depot over a period of time (at least 24 hours, 2 days, 3 days, 4 days, 5 days, 6 days, 1 week, 2 weeks, 3 weeks, 1 month, 2 months, 3 months, 4 months, 5 months or 6 months), rather than being dispersed immediately (e.g., at a diffusion-controlled rate) upon application or injection.

In some embodiment, the antibody that is able to activate gelation of the HA contains an IgG2 constant region. In some embodiment, the antibody that is able to activate gelation of the HA contains an IgG1 constant region. An IgG constant region includes, without limitation, a CH1, a CH2, and/or a CH3 fragment.

In some embodiments, the antibody is a human or humanized antibody. In some embodiments, the antibody is an anti-CSF1 (colony stimulating factor 1, or anti-CSF1R (colony stimulating factor 1 receptor) antibody. Example anti-CSF1 and anti-CSF1R antibodies are provided in Tables 1-2. Their sequences are provided in Tables 3A-B. In some embodiments, the antibody is AM001, PD-0360324, emactuzumab, IMC-CS4, or lacnotuzumab. In some embodiments, the antibody is AM001, which includes a heavy chain comprising the sequence of SEQ ID NO:7 and a light chain comprising the sequence of SEQ ID NO:8.

TABLE 1

Example Anti-CSF1R Antibodies

| Name | Other Names | Type | Computed pI (IPC protein) |
|---|---|---|---|
| Emactuzumab | RG7155, or RO5509554 | IgG1 humanized | 7.18 |
| Cabiralizumab | FPA008 | IgG4 humanized | 5.76 |
| Axatilimab | SNDX-6352 | IgG4 humanized | 5.92 |
| IMC-CS4 | LY3022855 | IgG1 human | 6.7 |
| AM001 | | IgG2 human | 6.2 |

TABLE 2

Example Anti-CSF1 Antibodies

| Name | Other Names | Type | Computed pI (IPC protein) |
|---|---|---|---|
| Lacnotuzumab | MCS110 | IgG1 human | 6.43 |
| PD-0360324 | | IgG2 human | 6.65 |

TABLE 3A

Sequences of Example Anti-CSF1R Antibodies

| Antibody | Protein Sequences |
|---|---|
| Emaduzumab (RG7155, or RO5509554) | Heavy chain (SEQ ID NO: 1)<br>QVQLVQSGAEVKKPGASVKVSCKASGYTFTSYDISWVRQAPGQGLEWMGVIWTDGGTNYA QKLQGRVTMTTDTSTSTAYMELRSLRSDDTAVYYCARDQRLYFDVWGQGTTVTVSSASTK GPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSRWQQGN VFSCSVMHEALHNHYTQKSLSLSPGK<br>Light chain (SEQ ID NO: 2)<br>DIQMTQSPSSLSASVGDRVTITCRASEDVNTYVSWYQQKPGKAPKLLIYAASNRYTGVPS RFSGSGSGTDFTLTISSLQPEDFATYYCQQSFSYPTFGQGTKLEIKRTVAAPSVFIFPPS DEQLKSGTASVVCLLNNFYPREAKVQWKVDNALQSGNSQESVTEQDSKDSTYSLSSTLTL SKADYEKHKVYACEVTHQGLSSPVTKSFNRGEC |
| Cabiralizumob (FPA008) | Heavy chain (SEQ ID NO: 3)<br>QVQLVQSGAEVKKPGSSVKVSCKASGYTFTDNYMIWVRQAPGQGLEWMGDINPYNGGTTF NQKFKGRVTITADKSTSTAYMELSSLRSEDTAVYYCARESPYFSNLYVMDYWGQGTLVTV SSASTKGPSVFPLAPCSRSTSESTAALGCLVKDYFPEPVTVSWNSGALTSGVHTFPAVLQ SSGLYSLSSVVTVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSRLTVDKSRWQ EGNVFSCSVMHEALHNHYTQKSLSLSLGK<br>Light chain (SEQ ID NO: 4)<br>EIVLTQSPATLSLSPGERATLSCKASQSVDYDGDNYMNWYQQKPGQAPRLLIYAASNLES GIPARFSGSGSGTDFTLTISSLEPEDFAVYYCHLSNEDLSTFGGGTKVEIKRTVAAPSVF IFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |

TABLE 3A-continued

Sequences of Example Anti-CSF1R Antibodies

| Antibody | Protein Sequences |
|---|---|
| IMC-CS4 (LY3022855) | Heavy chain (SEQ ID NO: 5)<br>QDQLVESGGGVVQPGRSLRLSCAASGFTFSSYGMHWVRQAPGEGLEWVAVIWYDGSNKYY<br>ADSVKGRFTISRDNSKNTLYLQMNSLRAEDTAVYYCARGDYEVDYGMDVWGQGTTVTVAS<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKTHTCPPCPAPELLGG<br>PSVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSREE<br>MTKNQVSLTCLVKGFYPSDIAVEWESNGQPENNYKTTPPVLDSDGSFFLYSKLTVDKSRW<br>QQGNVFSCSVMHEALHNHYTQKSLSLSPGK<br>Light chain (SEQ ID NO: 6)<br>AIQLTQSPSSLSASVGDRVTITCRASQGISNALAWYQQKPGKAPKLLIYDASSLESGVPS<br>RFSGSGSGTDFTLTISSLQPEDFATYYCQQFNSYPWTFGQGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| AM001 | Heavy chain (SEQ ID NO: 7)<br>QVQLVQSGAEVKKPGASVKVSCKASGYTFTSYGISWVRQAPGQGLEWMGWISAYNGNTNY<br>AQKLQGRVTMTTDTSTSTAYMELRSLRSDDTAVYYCARESWFGEVFFDYWGQGTLVTVSS<br>ASTKGPSVFPLAPCSRSTSESTAALGCLVKDYFPEPVTVSWNSGALTSGVHTFPAVLQSS<br>GLYSLSSVVTVPSSNFGTQTYTCNVDHKPSNTKVDKTVERKCCVECPPCPAPPVAGPSVF<br>LFPPKPKDTLMISRTPEVTCVVVDVSHEDPEVQFNWYVDGVEVHNAKTKPREEQFNSTFR<br>VVSVLTVVHQDWLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQGN<br>VFSCSVMHEALHNHYTQKSLSLSPGK<br>Light chain (SEQ ID NO: 8)<br>DIVMTQSPDSLAVSLGERATINCKSSQSVLDSSDNKNYLAWYQQKPGQPPKLLIYWASNR<br>ESGVPDRFSGSGSGTDFTLTISSLQAEDVAVYYCQQYYSDPFTFGPGTKVDIKRTVAAPS<br>VFIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |
| Axatilimab (SNDX-6352) | Heavy chain (SEQ ID NO: 9)<br>EVTLKESGPALVKPTQTLTLTCTFSGFSLTTYGMGVGWIRQPPGKALEWLANIWWDDDKY<br>YNPSLKNRLTISKDTSKNQVVLTMTNMDPVDTATYYCARIGPIKYPTAPYRYFDFWGQGT<br>MVTVSSASTKGPSVFPLAPCSRSTSESTAALGCLVKDYFPEPVTVSWNSGALTSGVHTFP<br>AVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREE<br>QFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDK<br>SRWQEGNVFSCSVMHEALHNHYTQKSLSLSLGK<br>Light chain (SEQ ID NO: 10)<br>DIQMTQSPSSLSASVGDRVTITCLASEDIYDNLAWYQQKPGKAPKLLIYYASSLQDGVPS<br>RFSGSGSGTDYTLTISSLQPEDFATYYCLQDSEYPWTFGGGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |

TABLE 3B

Sequences of Example Anti-CSF1 Antibodies

| Antibody | Protein Sequences |
|---|---|
| Lacnotuzumab (MCS110) | Heavy chain (SEQ ID NO: 11)<br>QVQLQESGPGLVKPSQTLSLTCTVSDYSITSDYAWNWIRQFPGKGLEWMGYISYSGSTSY<br>NPSLKSRITISRDTSKNQFSLQLNSVTAADTAVYYCASFDYAHAMDYWGQGTTVTVSSAS<br>TKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRVEPKSCDKTHTCPPCPAPELLGGPS<br>VFLFPPKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPSREEMT<br>KNQVSLTCLVKGFYPSDIAVEWESNGQPENNYKTTPPVLDSDGSFFLYSKLTVDKSRWQQ<br>GNVFSCSVMHEALHNHYTQKSLSLSPGK<br>Light chain (SEQ ID NO: 12)<br>DIVLTQSPAFLSVTPGEKVTFTCQASQSIGTSIHWYQQKTDQAPKLLIKYASESISGIPS<br>RFSGSGSGTDFTLTISSVEAEDAADYYCQQINSWPTTFGGGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| MCS110 var | Heavy chain (SEQ ID NO: 13)<br>DVQLQESGPGLVKPSQSLSLTCTVTDYSITSDYAWNWIRQFPGNKLEWMGYISYSGSTSY<br>NPSLKSRISITRDTSKNQFFLQLNSVTTEDTATYYCASFDYAHAMDYWGQGTSVTVSSAK<br>TTAPSVYPLAPVCGDTTGSSVTLGCLVKGYFPEPVTLTWNSGSLSSGVHTFPAVLQSDLY<br>TLSSSVTVTSSTWPSQSITCNVAHPASSTKVDKKIEPRGPTIKPCPPCKCPAPNLLGGPS<br>VFIFPPKIKDVLMISLSPIVTCVVVDVSEDDPDVQISWFVNNVEVHTAQTQTHREDYNST<br>LRVVSALPIQHQDWMSGKEFKCKVNNKDLPAPIERTISKPKGSVRAPQVYVLPPPEEEMT<br>KKQVTLTCMVTDFMPEDIYVEWTNNGKTELNYKNTEPVLDSDGSYFMYSKLRVEKKNWVE<br>RNSYSCSVVHEGLHNHHTTKSFSRTPG |

TABLE 3B-continued

Sequences of Example Anti-CSF1 Antibodies

| Antibody | Protein Sequences |
|---|---|
| PD-0360324 | Light chain (SEQ ID NO: 14)<br>DILLTQSPAILSVSPGERVSFSCRASQSIGTSIHWYQQRTNGSPRLLIKYASESISGIPS<br>RFSGSGSGTDFTLSINSVESEDIADYYCQQINSWPTTFGGGTKLEIKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSFNRNEC<br>Heavy chain (SEQ ID NO: 15)<br>EVQLVESGGGLVQPGGSLRLSCAASGFTFSSFSMTWVRQAPGKGLEWVSYISSRSSTISY<br>ADSVKGRFTISRDNAKNSLYLQMNSLRDEDTAVYYCARDPLLAGATFFDYWGQGTLVTVS<br>SASTKGPSVFPLAPCSRSTSESTAALGCLVKDYFPEPVTVSWNSGALTSGVHTFPAVLQS<br>SGLYSLSSVVTVPSSNFGTQTYTCNVDHKPSNTKVDKTVERKCCVECPPCPAPPVAGPSV<br>FLFPPKPKDTLMISRTPEVTCVVVDVSHEDPEVQFNWYVDGVEVHNAKTKPREEQFNSTF<br>RVVSVLTVVHQDWLNGKEYKCKVSNKGLPAPIEKTISKTKGQPREPQVYTLPPSREEMTK<br>NQVSLTCLVKGFYPSDIAVEWESNGQPENNYKTTPPMLDSDGSFFLYSKLTVDKSRWQQG<br>NVFSCSVMHEALHNHYTQKSLSLSPGK<br>Light chain (SEQ ID NO: 16)<br>EFVLTQSPGTLSLSPGERATLSCRASQSVSSSYLAWYQQKPGQAPRLLIYGASSRATGIP<br>DRFSGSGSGTDFTLTISRLEPEDFAVYYCQQYGSSPLTFGGGTKVEIKRTVAAPSVFIFP<br>PSDEQLKSGTASVVCLLNNFYPREAKVQWKVDNALQSGNSQESVTEQDSKDSTYSLSSTL<br>TLSKADYEKHKVYACEVTHQGLSSPVTKSFNRGEC |

Emactuzumab (also known as RG7155 and R05509554) is a clinical stage humanized IgG1 CSF1R targeted antibody designed to target and deplete macrophages in the tumor tissue. It has shown a favorable safety profile in patients and encouraging efficacy for TGCT. Emactuzumab is under investigation in clinical trial NCT01494688—"A Study of R05509554 as Monotherapy and in Combination with Paclitaxel in Participants With Advanced Solid Tumors."

Cabiralizumab (also known as FPA008) is under investigation in clinical trial NCT03502330—"APX005M With Nivolumab and Cabiralizumab in Advanced Melanoma, Non-small Cell Lung Cancer or Renal Cell Carcinoma." Cabiralizumab is a humanized IgG4 anti-CSF1R monoclonal antibody with a single amino acid substitution in the hinge region to prevent hemi-dimer exchange.

IMC-CS4 (also known as LY3022855) is a human IgG1 antibody (mAb) targeting CSF1R. IMC-CS4 is under investigation in clinical trial NCT01346358—"A Study of IMC-CS4 in Subjects With Advanced Solid Tumors."

AM001 is a fully human IgG2 anti-CSF1R antibody. Other example anti-CSF1R antibodies include PD-0360324 and GTX128677, without limitation.

Axatilimab (also known as SNDX-6352) is a humanized, full-length IgG4 antibody with high affinity to CSF-1R. Axatilimab affects the migration, proliferation, differentiation, and survival of monocytes and macrophages by binding to CSF-1R and blocking its activation by its two known ligands, CSF-1 and IL-34. Axatilimab is currently being evaluated in a Phase ½ clinical trial in patients with cGVHD.

Lacnotuzumab (also known as MCS110) is a high-affinity human engineered IgG1 anti-CSF1 antibody that blocks the ability of CSF1R to drive proliferation in responsive cells. Lacnotuzumab is under investigation in clinical trial NCT01643850—"MCS110 in Patients With Pigmented Villonodular Synovitis (PVNS)."

PD-0360324 is a fully human immunoglobulin G2 monoclonal antibody against CSF1 investigated for treating cutaneous lupus erythematosus (CLE). It is also being tested for its combination with Cyclophosphamide in treating patients with recurrent high-grade epithelial ovarian, primary peritoneal, or fallopian tube cancer.

The composition to be administered, in some embodiments, includes a minimum concentration of the antibody. In some embodiments, the minimum concentration is 2 mg/mL, or 5 mg/mL, 10 mg/mL, 15 mg/mL, 20 mg/mL, 25 mg/mL, 30 mg/mL, 40 mg/mL, 50 mg/mL, 75 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or 250 mg/mL.

In some embodiments, the composition to be administered is adjusted to have a suitable pH. In one embodiment, the pH is 4 to 10, 4 to 9.5, 4 to 9, 4 to 8.5, 4 to 8, 4 to 7.5, 4 to 7, 4 to 6.5, 4 to 6, 4 to 5.5, 4 to 5, 4.5 to 10, 4.5 to 9.5, 4.5 to 9, 4.5 to 8.5, 4.5 to 8, 4.5 to 7.5, 4.5 to 7, 4.5 to 6.5, 4.5 to 6, 4.5 to 5.5, 4.5 to 5, 4.9 to 10, 4.9 to 9.5, 4.9 to 9, 4.9 to 8.5, 4.9 to 8, 4.9 to 7.5, 4.9 to 7, 4.9 to 6.5, 4.9 to 6, 4.9 to 5.5, 5.5 to 10, 5.5 to 9.5, 5.5 to 9, 5.5 to 8.5, 5.5 to 8, 5.5 to 7.5, 5.5 to 7, 5.5 to 6.5, 5.5 to 6, 6 to 10, 6 to 9.5, 6 to 9, 6 to 8.5, 6 to 8, 6 to 7.5, 6 to 7, 6 to 6.5, 6.5 to 10, 6.5 to 9.5, 6.5 to 9, 6.5 to 8.5, 6.5 to 8, 6.5 to 7.5, 6.5 to 7, 7 to 10, 7 to 9.5, 7 to 9, 7 to 8.5, 7 to 8, 7 to 7.5, 7.5 to 10, 7.5 to 9.5, 7.5 to 9, 7.5 to 8.5, 7.5 to 8, 8 to 10, 8 to 9.5, 8 to 9, 8 to 8.5, 8.5 to 10, 8.5 to 9.5, 8.5 to 9, 9 to 10, 9 to 9.5, or 9.5 to 10. In one embodiment, the pH is 4.9 to 5.5.

In some embodiments, the composition administered, e.g., aqueous solution, has a pH that is at least 0.1, 0.2, 0.3, 0.4, 0.5, 0.6, 0.7, 0.8, 0.9, 1.0, 1.1, 1.2, 1.3, 1.4 or 1.5 lower than its pI. In some embodiments, the composition administered, e.g., aqueous solution, has a pH that is 0.1-2.5, 0.2-2.0, 0.3-1.5, 0.5-1.5, 0.6-1.4, 0.7-1.3, 0.8-1.2, or 0.9-1.1 lower than its pI.

The pI of an antibody can be readily tested in the lab, or estimated with computational methods. An example computational method is descried in Kozlowski LP (2016) "IPC—Isoelectric Point Calculator," *Biology Direct* 11:55, with a free program online at isoelectric.org. The pI's of the disclosed antibodies are provided in Tables 1-2, which were calculated using the online tool, using the "IPC Protein" parameters.

Emactuzumab has a calculated pI of 7.18. In some embodiments, the pH of the composition or solution that includes Emactuzumab is 5.5 to 6.5, such as 5.6 to 6.5, 5.7 to 6.45, 5.8 to 6.45, 5.9 to 6.45, 6 to 6.45, 6.1 to 6.45, 6.2 to 6.4, 6.25 to 6.35, or 6.28 to 6.32, without limitation.

Cabiralizumab has a calculated pI of 5.76. In some embodiments, the pH of the composition or solution that includes Cabiralizumab is 4.0 to 5.3, such as 4.1 to 5.2, 4.2 to 5.0, 4.3 to 4.9, 4.4 to 4.8, 4.5 to 4.8, 4.5 to 4.7, or 4.6 to 4.7, without limitation.

Axatilimab has a calculated pI of 5.92. In some embodiments, the pH of the composition or solution that includes Axatilimab is 4.0 to 5.4, such as 4.1 to 5.4, 4.2 to 5.3, 4.3 to 5.2, 4.4 to 5.0, 4.5 to 5.0, 4.6 to 5.0, or 4.7 to 4.9, without limitation.

IMC-CS4 has a calculated pI of 6.7. In some embodiments, the pH of the composition or solution that includes IMC-CS4 is 5.0 to 6.3, such as 5.1 to 6.2, 5.2 to 6.0, 5.3 to 5.9, 5.4 to 5.8, 5.5 to 5.8, 5.5 to 5.7, or 5.6 to 5.7, without limitation.

AM001 has a calculated pI of 6.2. In some embodiments, the pH of the composition or solution that includes AM001 is 4.5 to 5.5, such as 4.6 to 5.5, 4.7 to 5.45, 4.8 to 5.45, 4.9 to 5.4, 5 to 5.4, 5.1 to 5.35, 5.1 to 5.3, 5.1 to 5.25, or 5.1 to 5.2, without limitation.

Lacnotuzumab has a calculated pI of 6.43. In some embodiments, the pH of the composition or solution that includes Lacnotuzumab is 4.9 to 5.9, such as 5.1 to 5.8, 5.2 to 5.8, 5.3 to 5.7, or 5.4 to 5.6 without limitation.

PD-0360324 has a calculated pI of 6.65. In some embodiments, the pH of the composition or solution that includes PD-0360324 is 4.9 to 6.2, such as 5.2 to 6.1, 5.2 to 5.9, 5.3 to 5.8, or 5.5 to 5.7 without limitation.

In some embodiments, the composition does not include high levels of excipients with high ionic strength, such as alkaline salts and salts of amino acids. Examples include NaCl, KCl, $CaCl_2$, salts of arginine, without limitation. In some embodiments, the concentration of alkaline salts and salts of amino acids (excluding histidine), if present, is not higher than 100 mM, 90 mM, 80 mM, 70 mM, 60 mM, 50 mM, 40 mM, 30 mM, 20 mM, 15 mM, 10 mM, 5 mM, 2 mM, 1 mM, 0.5 mM or 0.1 mM.

In some embodiments, the composition includes HA, such as at a concentration that is 0.05 to 2 w/v %, 0.1 to 1.5 w/v %, 0.1 to 1.2 w/v %, 0.1 to 1 w/v %, 0.1 to 0.9 w/v %, 0.15 to 0.8 w/v %, 0.15 to 0.7 w/v %, 0.15 to 0.6 w/v %, 0.2 to 0.5 w/v %, 0.2 to 0.4 w/v %, 0.25 to 0.35 w/v %, or 0.28 to 0.32 w/v %, without limitation.

In some embodiments, the composition further includes other ingredients as disclosed below, which forms an extended release formulation.

III. Antibody Formulations

Formulations containing the antibodies of the present disclosure are also provided. In one embodiment, provided is a composition that includes at least 15 mg/mL of an antibody, 0.1 to 1.5 w/v % hyaluronic acid (HA), and water. In some embodiments, the composition has a pH that is at least 0.5 below the isoelectric point (pI) of the antibody. In some embodiments, the antibody is embedded in a gel comprising the HA.

In some embodiments, the composition has a pH that is at least 0.1, 0.2, 0.3, 0.4, 0.5, 0.6, 0.7, 0.8, 0.9, 1.0, 1.1, 1.2, 1.3, 1.4 or 1.5 lower than the pI of the antibody. In some embodiments, the composition has a pH that is 0.1-2.5, 0.2-2.0, 0.3-1.5, 0.5-1.5, 0.6-1.4, 0.7-1.3, 0.8-1.2, or 0.9-1.1 lower than the pI. The pI of an antibody can be readily tested in the lab, or estimated with computational methods. The pI's of the disclosed antibodies are provided in Tables 1-2.

Emactuzumab has a calculated pI of 7.18. In some embodiments, the pH of the composition or solution that includes Emactuzumab is 5.5 to 6.5, such as 5.6 to 6.5, 5.7 to 6.45, 5.8 to 6.45, 5.9 to 6.45, 6 to 6.45, 6.1 to 6.45, 6.2 to 6.4, 6.25 to 6.35, or 6.28 to 6.32, without limitation.

Cabiralizumab has a calculated pI of 5.76. In some embodiments, the pH of the composition or solution that includes Cabiralizumab is 4.0 to 5.3, such as 4.1 to 5.2, 4.2 to 5.0, 4.3 to 4.9, 4.4 to 4.8, 4.5 to 4.8, 4.5 to 4.7, or 4.6 to 4.7, without limitation.

Axatilimab has a calculated pI of 5.92. In some embodiments, the pH of the composition or solution that includes Axatilimab is 4.0 to 5.4, such as 4.1 to 5.4, 4.2 to 5.3, 4.3 to 5.2, 4.4 to 5.0, 4.5 to 5.0, 4.6 to 5.0, or 4.7 to 4.9, without limitation.

IMC-CS4 has a calculated pI of 6.7. In some embodiments, the pH of the composition or solution that includes IMC-CS4 is 5.0 to 6.3, such as 5.1 to 6.2, 5.2 to 6.0, 5.3 to 5.9, 5.4 to 5.8, 5.5 to 5.8, 5.5 to 5.7, or 5.6 to 5.7, without limitation.

AM001 has a calculated pI of 6.2. In some embodiments, the pH of the composition or solution that includes AM001 is 4.5 to 5.5, such as 4.6 to 5.5, 4.7 to 5.45, 4.8 to 5.45, 4.9 to 5.4, 5 to 5.4, 5.1 to 5.35, 5.1 to 5.3, 5.1 to 5.25, or 5.1 to 5.2, without limitation.

Lacnotuzumab has a calculated pI of 6.43. In some embodiments, the pH of the composition or solution that includes Lacnotuzumab is 4.9 to 5.9, such as 5.1 to 5.8, 5.2 to 5.8, 5.3 to 5.7, or 5.4 to 5.6 without limitation.

PD-0360324 has a calculated pI of 6.65. In some embodiments, the pH of the composition or solution that includes PD-0360324 is 4.9 to 6.2, such as 5.2 to 6.1, 5.2 to 5.9, 5.3 to 5.8, or 5.5 to 5.7 without limitation.

In some embodiments, the composition does not include high levels of excipients with high ionic strength, such as alkaline salts and salts of amino acids. Examples include NaCl, KCl, $CaCl_2$, salts of arginine, without limitation. In some embodiments, the concentration of alkaline salts and salts of amino acids (excluding histidine), if present, is not higher than 100 mM, 90 mM, 80 mM, 70 mM, 60 mM, 50 mM, 40 mM, 30 mM, 20 mM, 15 mM, 10 mM, 5 mM, 2 mM, 1 mM, 0.5 mM or 0.1 mM.

In some embodiments, the composition includes HA, such as at a concentration that is 0.05 to 2 w/v %, 0.1 to 1.5 w/v %, 0.1 to 1.2 w/v %, 0.1 to 1 w/v %, 0.1 to 0.9 w/v %, 0.15 to 0.8 w/v %, 0.15 to 0.7 w/v %, 0.15 to 0.6 w/v %, 0.2 to 0.5 w/v %, 0.2 to 0.4 w/v %, 0.25 to 0.35 w/v %, or 0.28 to 0.32 w/v %, without limitation.

In some embodiments, provided is a pharmaceutical composition for local administration, providing controlled release of the therapeutic agent in the pharmaceutical composition. The controlled release excipient may be a gel-forming excipient, in particular, when the therapeutic agent is a large molecule such as an antibody. Preferred gel-forming excipients are thermogels. The controlled release excipient may be a biodegradable matrix. Preferably, a biodegradable matrix is formulated as microspheres for delivery of small molecule therapeutic agent. The composition may be formulated for injection. The therapeutic agent, in some embodiments, is an antibody of the present disclosure.

Controlled release may provide sustained release of a therapeutic agent, extending for hours, days or months, or may provide pulsatile release of the therapeutic agent, and may vary as a function of numerous factors. The rate of release may depend on factors including the type and the concentration of the therapeutic agent and the excipient in the composition and location of administration.

In some embodiments, the composition comprises about 1% w/w to about 90% w/w, or about 5% w/w to about 80% w/w, or about 10% w/w to about 70% w/w of the antibody based on the total weight of the composition. In some embodiments, the composition comprises about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% w/w of the antibody based on the total weight of the composition, or within any range between any two of the values, end points inclusive.

In some embodiments, the antibody is released from the composition in a controlled manner (e.g., releasing a daily therapeutic amount each day) over a period of time, such as 1 day, 2 days, 1 week, 2 weeks, 3 weeks, 6 weeks, 1 month, 2 months, 3 months or 6 months. In some embodiments, each administration results in sustained exposure of the antibody for at least 3 weeks, 4 weeks, 2 months, 3 months, 4 months, or 6 months. In some embodiments, the effective amount is for local administration and is less than that needed for systemic administration, such as, equal to or less than 90%, equal to or less than 80%, equal to or less than 70%, equal to or less than 60%, equal to or less than 50%, equal to or less than 40%, equal to or less than 30%, equal to or less than 20%, equal to or less than 10%, equal to or less than 5%, or equal to or less than 1%, of a corresponding effective amount for systemic administration, or any range between any of the two numbers, endpoints inclusive.

In some embodiments, the composition is a controlled release formulation that releases the antibody to provide a therapeutically effective amount over an extended period of time. In some embodiments, the composition releases a therapeutically effective amount of antibody inhibitor for 1 week, 2 weeks, 3 weeks, 1 month, 2 months, 3 months, or 6 months. In preferred embodiments, the controlled release formulations provide therapeutically effective amounts of the antibody when administered once or twice monthly.

In some embodiments, the composition is a controlled release formulation that contains a mixture of microparticles designed to release the antibody at different times. For example, the composition may release the antibody in a pulsatile mode where different populations of microparticles are designed to release therapeutic doses as discrete bursts over a prespecified time.

In some embodiments, the gel-forming excipient is a thermogel having a transition temperature of above room temperature but below or at body temperature. In this embodiment, the formulation is an injectable liquid at room temperature that converts to a gel phase after administration. In some embodiments, the composition has a transition temperature of about 25° C. to about 36° C. or about 28° C. to about 35° C. Upon conversion to a gel phase after administration, the therapeutic agent is released slowly from the gel, allowing therapeutic effect. In some embodiments, the thermogel is biodegradable.

A gel-forming excipient may provide sustained release of the therapeutic agent by forming a gel upon administration, such as is the case with thermogels, or by enhancing the viscosity of the formulation. Gel-forming excipients include polymers selected from poloxamer, hyaluronic acid (HA), alginate, hydroxy methylcellulose (HPMC), hydroxy propylcellulose (HPC), sodium carboxymethylcellulsoe (NaCMC) or polyvinyl povidone (PVP). In some embodiment the composition comprises a viscosity enhancing agent such as NaCMC, hydroxypropyl cellulose (HPC), or polyvinyl pyrrolidone (PVP).

In some embodiments the polymer encapsulates the active ingredient in microspheres or nanospheres and comprises a biodegradable material such as poly(D,L-lactic acid) (PLA), poly(D,L-lactic-co-glycolic acid) (PLGA), or a block copolymer comprising hydrophilic poly(ethylene glycol) (PEG) and one or more polymers selected from poly(lactic acid-co-glycolic acid) (PLGA), poly(ε-caprolactone) (PCL), and poly(ε-caprolactone-co-glycolic acid) (PCGA), such as poly (ε-caprolactone-co-glycolic acid)-poly(ethylene glycol)-poly(ε-caprolactone-co-glycolic acid) (PCGA-PEG-PCGA) and poly(lactic acid-co-glycolic acid)-poly(ethylene glycol)-poly(lactic acid-co-glycolic acid) (PLGA-PEG-PLGA), or a combination thereof. Long-chain or medium chain triglycerides may be incorporated into the microshperes or nanosperes to further enhance stability and/or drug release from the microspheres or nanospheres. See, e.g., Meng, B, et al., Int'l J. Pharm., Vol 397 (1-2), 136-142 (2010).

In some embodiments, the composition comprises about 5% to about 50% of the gel-forming excipient based on the total weight of the composition. In some embodiments, the composition comprises about 5%, 10%, 15%, 20%, 25%, 30%, 35%, 40%, 45% or 50% of the gel-forming excipient based on the total weight of the composition, or any range between any two of the values, endpoints inclusive.

In some embodiments, the thermogel comprises hyaluronic acid (HA) or a pharmaceutically acceptable salt thereof. Hyaluronic acid is a mucopolysaccharide consisting of N-acetylglucosamine and glucuronic acid. The pharmaceutically acceptable salts of HA include the salts with lithium, sodium, potassium, magnesium, calcium and the like. In some embodiments, HA or its pharmaceutically acceptable salt has a molecular weight of about $2\times10^5$ to $5\times10^6$ Daltons, or about $5\times10^5$ to $3\times10^6$ Daltons, or about $7\times10^5$ to $2.5\times10^6$ Daltons. In some embodiments, the composition comprises about 5%, 10%, 15%, 20%, 25%, 30%, 35%, 40%, 45% or 50% HA.

In some embodiments, the thermogel comprises a poloxamer. Poloxamers are biocompatible polyoxyethylene-polyoxypropylene block copolymers that are also known by their tradenames such as Pluronics® and Lutrol®. There are several types of poloxamers based on the molecular weight and the amount of oxyethylene and oxypropylene units, for example, poloxamers 124, 182, 188, 237, 338 and 407. When dissolved in water or an aqueous solvent, they form a thermogel.

In some embodiments, the thermogel comprises about 25% to 33% of poloxamer 407 or poloxamer 188, or a combination thereof, and an aqueous solvent, such as water or an aqueous buffer. In some embodiments, the thermogel comprises about 25% to 33% of a mixture of poloxamer 407 or poloxamer 188 in a ratio of between 3:1 and 0.8:1.

In some embodiments, the composition comprises a biodegradable matrix. The biodegradable matrix comprises a biodegradable polymer. Examples of biodegradable polymers include, but are not limited to, polycyanoacrylates, polyurethanes, polyorthoester, polyacetals, polyesters, such as poly(D,L-lactic acid) (PLA) and poly(D,L-lactic-co-glycolic acid) (PLGA), poly hydroxyl butyrate, polyester, polycaprolactone, poly lactide-co-glycolide (PLGA), and poly diaxonone; polyanhydride, such as poly adepic acid, poly sebacic acid, and poly terpthalic acid; polyamides, such as poly amino acid, and poly imino carbonate; phosphorous based polymer, such as polyphosphates, poly phosphonates, and poly phosphazenes. Other examples of biodegradable polymers include poly(ricinoleic acid) (RA); poly(fumaric acid) (FA); poly(fatty acid dimer) (FAD); poly(terephthalic acid) (TA); poly(isophthalic acid) (IPA); poly(p-{carboxyphenoxy}methane) (CPM); poly-{carboxyphenoxy}propane) (CPP); poly(p-{carboxyphenoxy}hexane) (CPH); polyamines, polyesteramides, (CHDM: Cis/trans-cyclohexyl dimethanol, HD:1,6-hexanediol (3,9-diethylidene-2,4,8,10-tetraoxaspiro undecane) (DETOSU); polydioxanones; polyhydroxybutyrates; polyalkyene oxalates; polyketals; polycarbonates; polyorthocarbonates; polysiloxanes; succinates; hyaluronic acid; poly(malic acid); polyhydroxyvalerates; polyalkylene succinates; polyvinylpyrrolidone; polyacrylic acids; polybutyric acid: polyvaleric acid; and poly(glutamic acid-co-ethyl glutamate), copolymers and/or mixtures thereof. In some embodiments, the biodegradable matrix comprises PLA and/or PLGA microspheres.

Certain polymers are both biodegradable and can form a thermogel, for example, block copolymers of polyethylene oxide and poly(L-lactic acid).

In some embodiments, the therapeutic agent is formulated as a complex with a complexing agent such as a cyclodextrins or a resin, then formulated as microspheres. In this embodiment, the therapeutic agent is preferable a small molecule. The complexing agent prolongs release of the therapeutic agent. Formulations in which the therapeutic agent is formulated as microspheres with a complexing agent may optionally include a viscosity enhancing agent. In some embodiments, the cyclodextrin is hydroxypropyl-β-cyclodextrin or sulfobutyl ether-β-cyclodextrin.

As used herein, "microparticles" refers to particles having a diameter of less than 1 mm, more or less than 900 μm, 800 μm, 700 μm, 600 μm, 500 μm, 400 μm, 300 μm, 200 or 100 μm. Microparticles can be "microspheres", which are solid spherical microparticles, and microcapsules, which are spherical microparticles having a core of a different polymer, drug, or composition.

Many polymers can be used to prepare the microspheres for controlled drug delivery. Polymers typically are thermoplastic synthetic polymers, such as ethylene vinyl acetate and poly(acrylic acid), which are generally viewed as non-biodegradable since they remain in relatively the same form over a period of at least two or three years following implantation in the body, and biodegradable polymers, such as poly(hydroxy acids) including polylactic acid, polyglycolic acid, and copolymers thereof, polyanhydrides, polyorthoesters, and certain types of protein and polysaccharide polymers. A polymer may have a half-life in the biological environment of about 1 week to about 10 years, for example, about 1 week, about 1 month, about 6 months, about 1 year, about 5 years, about 10 years, or a range of values between any two of these.

An example polymer material is one which is biodegradable and which retains sufficient form to control release for a period following implantation of at least six to seven days. The poly (hydroxy acids), especially poly(lactic acid-co-glycolic acid) ("PLGA"), is a particularly useful polymer and has been used in the manufacture of degradable sutures for several decades. The polymer degrades by hydrolysis following exposure to the aqueous environment of the body. The polymer is hydrolyzed to yield lactic and glycolic acid monomers, which are normal byproducts of cellular metabolism. The rate of polymer disintegration can vary from several weeks to periods of greater than one year, depending on several factors including polymer molecular weight, ratio of lactide to glycolide monomers in the polymer chain, and stereoregularity of the monomer subunits (mixtures of L and D stereoisomers disrupt the polymer crystallinity enhancing polymer breakdown).

Particularly useful results can be obtained by blending PLGA having different molecular weights, and/or different ratios of lactide to glycolide. The molecular weight and monomer ratios can be optimized to tailor the release kinetics over a defined period of time. The higher molecular weights result in polymer matrices which retain their structural integrity for longer periods of time; while lower molecular weights, result in both faster release and shorter matrix lives.

In some embodiments, the microspheres contain blends of at least two and more preferably three or more biodegradable polymers, preferably hydrolytically unstable polymers, most preferably poly(hydroxy acids) of different molecular weight and/or monomer ratio. In a preferred embodiment, three different molecular weight PLGAs are blended to form a composition that has linear release over a defined period of time, ranging from at least one day to about sixty days. In a more preferred embodiment to obtain release from about one to twenty-one days, the PLGAs have molecular weights between 1000 and 20,000, more preferably between 5,000 and 10,000, between 20,000 and 35,000, more preferably between 25,000 and 30,000, and between 35,000 and 70,000, more preferably 5000 and 10,000. In the most preferred embodiment for release over a period of about one week, PLGAs having molecular weights of about 6,000, 30,000, and 41,000 are combined. In some embodiments, the microspheres may contain medium or long-chain triglycerides to enhance stability and/or drug release.

PLA polymers can be prepared from the cyclic esters of lactic acids. Both L(+) and D(-) forms of lactic acid can be used to prepare the PLA polymers, as well as the optically inactive DL-lactic acid mixture of D(-) and L(+) lactic acids. Methods of preparing polylactides are well documented in the patent literature.

Microsphere formulations may be prepared with combinations of different populations of microspheres as described herein. Each population of microspheres in the combination may be designed to release the therapeutic agent at different rates, thereby providing prolonged therapeutic effect. In some embodiments, the formulation provides a pulsatile release of the therapeutic agent by combining populations of micro spheres, wherein each population is designed to release the therapeutic agent in a single burst at prespecified periods of time.

In some embodiment the release retarding agent is a high molecular weight polymer that is covalently bound to the therapeutic agent to prolong the circulating half-life. For example, the therapeutic agent may be PEGylated with high molecular weight PEG. PEGylation is a preferred embodiment where the therapeutic agent is a large molecule such as an antibody.

In some embodiments, the therapeutic agent is administered locally via implantation of a depot drug delivery vehicle. Implantation will be at, inside the tumor or near the tumor site and may occur in connection with surgery to remove tumor mass. Depot drug delivery systems have been developed for implantation, providing localized drug delivery over an extended period of time. Such drug delivery systems can take several forms, including gels, films, wafers, rods and particles and are designed to provide predictable controlled release of the therapeutic agent. See Wolinski, J B, Colson, Y L, and Grinstaf, M W, J Control Release, 2012 Apr. 10: 159(1). Preferred implantable delivery systems are biodegradable polymers.

The polymers used in implantable delivery systems may be natural or synthetic. Natural polymeric systems include polysaccharides such as alginate, hyaluronic acid, dextran and chitosan, and polypeptides such as collagen, albumin, elastin and gelatin. Such polymeric delivery systems may form gels upon administration, and thereby provide prolonged local drug delivery. Synthetic polymers for drug depot implants are known and include polyesters based on lactide, glycolide, caprolactone, and dioxanone, polyanhydrides based on sebacic and adipic acid, and polyamides, polycarbonates, polyorthoesters and phosphate-based polymers. Synthetic polymeric systems are often hydrophobic and are well-suited to prolonged delivery of water-insoluble drugs.

In some embodiments, the formulation includes one or more tonicity agents. The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, or suspension that solubilize up on dilution, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof.

In some embodiments, the formulation includes one or more surfactants. As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical formulations and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic® F68 or Poloxamer 188™. Polyoxyethylene alkyl ethers include those sold under the trademark Brij™. Alkylphenolpolyoxyethylene ethers include those sold under the tradename Triton-X.

In some embodiments, the formulation further includes one or more antioxidants. An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates and inhibit other oxidation reactions by being oxidized themselves. As a result, antioxidants are often reducing agents, chelating agent and oxygen scavengers such as citrate, EDTA, DPTA, thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

In some embodiments, the formulation further includes one or more preservatives. A "preservative" is a natural or synthetic chemical that is added to products such as foods, pharmaceuticals, paints, biological samples, wood, etc. to prevent deformulation by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in parenteral proteins such as benzyl alcohol, phenol, m-cresol, chlorobutanol or methylparaben.

In some embodiment the formulation further includes buffering system such as citrate, acetate, borate, phosphate or combination of. In some embodiment the formulation further includes tertiary butanol to enhance property and stability of lyophilized material.

III. Methods of Administration

Methods of administration are also provided. In some embodiments, the administration is local to a tissue that is at or proximate to the site of a disease, such as inflammation or tumor. In some embodiments, the administration is intratumoral or at a site proximate to the tumor. In some embodiments, the tissue contains hyaluronic acid (HA) such as subcutaneous area or intramuscular (skeletal muscle).

In some embodiments, the tissue is in a hand. In some embodiments, the tissue is in a knee. In some embodiments, the tissue is in a digit joint. In some embodiments, the tissue is in a wrist. In some embodiments, the tissue is in a foot. In some embodiments, the tissue is in a hip. In some embodiments, the tissue is in an elbow. In some embodiments, the tissue is in an ankle. In some embodiments, the tissue is in a skin/dermal tissue. In some embodiments, the tissue is an ocular tissue. Accordingly, in some embodiments, the administration is injection, such as intraarticular injection, subcutaneous injection, intravitreal injection, or intramuscular injection.

In some embodiments, the tissue is under a skin. In some embodiments, the administration is subcutaneous. In some embodiments, the tissue is in an eye. In some embodiments, the administration is intravitreal injection. In some embodiments, multiple (2, 3, 4, or 5 or more) subcutaneous or intravitreal injections are performed for a particular patient. In some embodiments, the composition or formulation used in the subcutaneous injection has relatively high concentration of the antibody, such as at least 2 mg/mL, or 5 mg/mL, 10 mg/mL, 15 mg/mL, 20 mg/mL, 25 mg/mL, 30 mg/mL, 40 mg/mL, 50 mg/mL, 75 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, or 250 mg/mL. In some embodiments, given that the hyaluronic acid (HA) at the injection site helps create a sustained release profile, the injected composition itself does not need to be in an extended release form. In some embodiments, the injected composition does not include viscosity enhancing excipients or polymers.

In some embodiments, the composition to be administered is adjusted to have a suitable pH. In one embodiment, the pH is 4 to 10, 4 to 9.5, 4 to 9, 4 to 8.5, 4 to 8, 4 to 7.5, 4 to 7, 4 to 6.5, 4 to 6, 4 to 5.5, 4 to 5, 4.5 to 10, 4.5 to 9.5, 4.5 to 9, 4.5 to 8.5, 4.5 to 8, 4.5 to 7.5, 4.5 to 7, 4.5 to 6.5, 4.5 to 6, 4.5 to 5.5, 4.5 to 5, 4.9 to 10, 4.9 to 9.5, 4.9 to 9, 4.9 to 8.5, 4.9 to 8, 4.9 to 7.5, 4.9 to 7, 4.9 to 6.5, 4.9 to 6, 4.9 to 5.5, 5.5 to 10, 5.5 to 9.5, 5.5 to 9, 5.5 to 8.5, 5.5 to 8, 5.5 to 7.5, 5.5 to 7, 5.5 to 6.5, 5.5 to 6, 6 to 10, 6 to 9.5, 6 to 9, 6 to 8.5, 6 to 8, 6 to 7.5, 6 to 7, 6 to 6.5, 6.5 to 10, 6.5 to 9.5, 6.5 to 9, 6.5 to 8.5, 6.5 to 8, 6.5 to 7.5, 6.5 to 7, 7 to 10, 7 to 9.5, 7 to 9, 7 to 8.5, 7 to 8, 7 to 7.5, 7.5 to 10, 7.5 to 9.5, 7.5 to 9, 7.5 to 8.5, 7.5 to 8, 8 to 10, 8 to 9.5, 8 to 9, 8 to 8.5, 8.5 to 10, 8.5 to 9.5, 8.5 to 9, 9 to 10, 9 to 9.5, or 9.5 to 10. In one embodiment, the pH is 4.9 to 5.5.

In some embodiments, the tissue is near a site of TGCT. In some embodiments, the release occurs over a designate period of time. In some embodiments, the designate period of time is 1 week, 2 weeks, 3 weeks, 1 month, 2 months, 3 months, or 6 months. In some embodiments, the pharmaceutical composition is administered to the patient every week, every 2 weeks, every 3 weeks, every month, every 2 months, every 3 months, or every 6 months. In some embodiments, the frequency of administration is correlated to the designate period of time.

In some embodiments, the composition is administered at the tumor site. In some embodiments, the composition is administered proximate to the tumor site, such as equal to or less than 1 mm, equal to or less than 5 mm, equal to or less than 1 cm, equal to or less than 2 cm, or equal to or less than 5 cm from the tumor site. In a preferred embodiment, the pharmaceutical composition is administered by intra-articular injection into the impacted joint. In some embodiments, the pharmaceutical composition is administered by subcutaneous or intramuscular injection.

In some embodiments, the methods are for treating a patient having TGCT or other tumors (e.g., melanoma, glioblastoma, leukemia, and congenital hypertrichosis *lanuginosa* (CHL)) that can be suitably treated with CSF1/CSF1R inhibition.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Example 1. Hyaluronic Acid Precipitated AM001

This example screened for polymers that may be useful for preparing a hydrogel formulation for AM001, but surprisingly found that hyaluronic acid (HA) was able to form a gel like material which acted as a depot releasing the antibody slowly.

The following polymers were tested for their suitability for developing a slow-release formulation for AM001, poloxamer 407 (F127), poloxamer 188 (F68), hydroxypropyl methyl cellulose (low and high viscosity), and hyaluronic acid (HA, 1.0-1.5×10$^6$ kD). The antibody AM001 was prepared in water (WFI) containing 10 mM acetic acid, 9% sucrose (w/v), 0.004% PS-20 (w/v), and 0.1N NaOH to adjust the pH to 4.9-5.5.

It was discovered that when 1 mg/mL hyaluronic acid (HA)+15% poloxamer 407 (407) were added to 15 mg/mL AM001, the samples formed a small lump of wax-like material (FIG. 1). The wax-like material was observed both before and after three freeze-thaw cycles (FT), but not in samples in which only 407 was added.

Figure 2:
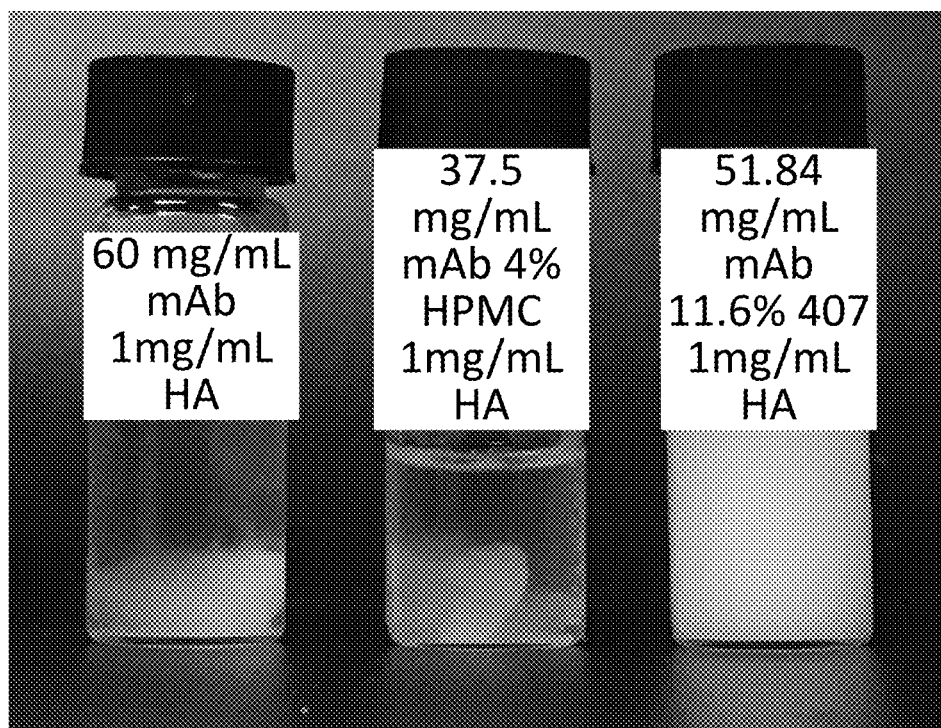
FIG. 2 shows that HA precipitated AM001 alone, or with HPMC or poloxamer 407.
Figure 3:
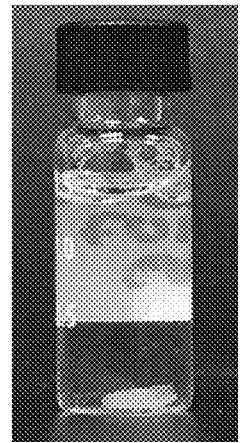
FIG. 3 shows precipitation of AM001, in the presence of HA and 407, became more visible after dilution.

To confirm that the HA was able to gel in the presence of AM001 (51.84 mg/mL), HA stock solution was added to a final concentration of 1 mg/mL to the AM001 solution with or without other polymers. As shown in FIG. 2, 1 mg/mL HA precipitated AM001 alone, or with HPMC or poloxamer 407. The precipitation became more visible after the mixture (HA/407/AM001) was diluted to 2 mg/mL AM001 (FIG. 3). Further dilution, however, was able to dissolve the precipitation, showing that the precipitation was reversible.

In vitro release study was performed to measure the release of the antibody from the mixture into simulated synovial fluid. The antibody was released slowly at rate of about 2-5% per 24 hr.

Another experiment showed that, unlike AM001, antibody pembrolizumab (IgG4 antibody) did not trigger gelation of hyaluronic acid (HA).

This example, therefore, demonstrates that AM001 can trigger HA gelation. This was unexpected as, to the best knowledge of the inventors, there has been no report that antibodies can trigger gelation of HA. Also unexpected is that such gelation was reversible.

Example 2. Gelation of Endogenous Hyaluronic Acid by AM001 In Vivo

This example shows that injected AM001 triggered gelation of endogenous hyaluronic acid (HA) in vivo.

An aqueous AM001 solution (30 mg/mL AM001, 10 mM acetic acid, 9% sucrose (w/v), 0.004% PS-20 (w/v), with 0.1N NaOH to adjust the pH to 4.9-5.5) was administered, intra-articularly, to the joints of monkeys. It was observed that gel-like materials formed with hyaluronic acid (HA) in the joints, while no such gel was seen with the vehicle alone.

Example 3. PK and PD of AM001 Following Subcutaneous Administration

This experiment was conducted to evaluate the pharmacokinetics (PK) and pharmacodynamics of a single subcutaneous (SC) 4 mg/kg dose of AM001 in healthy adult subjects.

Methodology: This was a Phase 1, single-center, open-label (unblinded) study. Each of 8 subjects (4 males, 4 females) received a single SC dose of 4 mg/kg AM001. The dosing volume was approximately 0.06 ml/kg of a 70 mg/ml drug product formulation with a pH of 5.2.

Subjects resided at the study center from Day −1 (the day before study drug dosing) to Day 8 (168 hours post-dose). On Day 1, subjects received the anti-CSF1R mAb, AM001. Blood samples for serum pharmacokinetic analysis of AM001 levels were collected pre-dose and at 3, 9, 24, 48, 72, 96, 120, 168 hours post-dose while the subject is residing at the study center. Analysis of serum CSF1 levels at the same time points was also performed as a measure of in vivo AM001 pharmacologic activity—hence, a pharmacodynamic marker. Specifically, the mAb inhibits binding of the natural CSF1 ligand to its receptor and thus results in elevated CSF1 levels when present at effective levels. Subjects returned to the study center for PK sampling timepoints at 240, 336, and 504 hours post-dose. Serum AM001 and CSF1 levels were analyzed by sensitive ELISA methodology.

Figure 4:
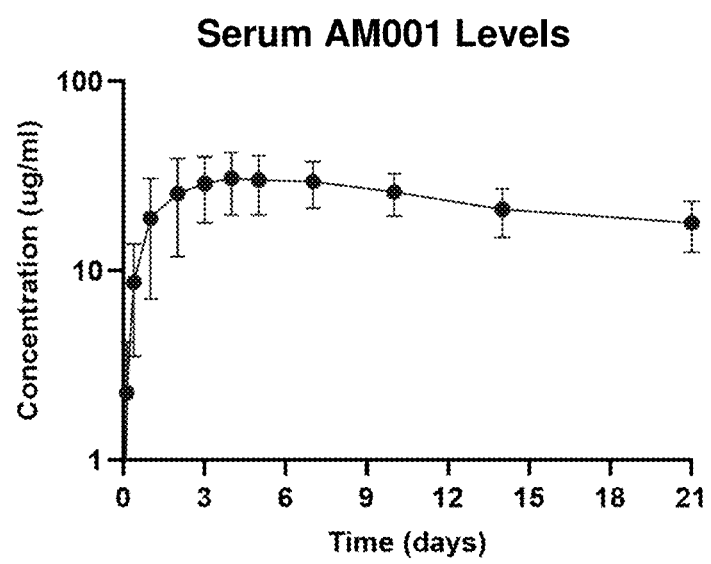
FIG. 4 shows the serum levels of AM001 (PK) following subcutaneous injection.
Figure 5:
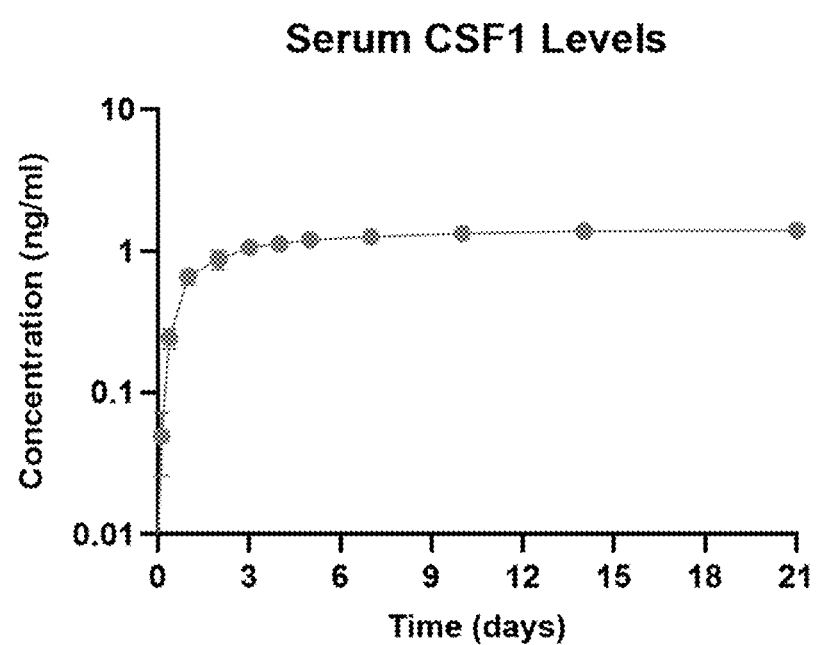
FIG. 5 shows the serum levels of CSF1 following subcutaneous injection of AM001.

Results: Mean+/−SD serum AM001 (PK) or CSF1 (PD) levels are shown in FIGS. 4 and 5. The pharmacokinetic profile demonstrates high bioavailability, sustained drug release, and a long half-life (>1=22 days) exceeding expectations from published human IV PK profiles and typical SC serum concentration vs time antibody profiles.

The observed pharmacodynamic profile indicates a rapid onset of CSF1R inhibitory activity with complete plateau—indicative of full activity within a week of dosing which actually did not decay at all through the 3-week monitored period. Hence, AM001 SC pharmacodynamics clearly extend beyond its pharmacokinetics.

It is contemplated that such superior pharmacodynamics and pharmacokinetics are at least in part attributed to the ability of AM001 to trigger gelation of hyaluronic acid, which is present at or near the site of the subcutaneous injection. These data support a long-acting (likely well over 1 month) drug candidate and drug formulation at this dose and likely many others.

Example 4. Testing of Suitable Gelation Conditions in HA

This example tested the gelation of AM001 in the presence of HA under different conditions.

A. 5% Dextrose vs. Normal Saline

AM001 was diluted to 30 mg/mL with either normal saline or 5% dextrose (Drug Product (DP): AM001 70 mg/mL in 10 mM acetate (pH 5.2) and 260 mM sucrose). Diluted AM001 was injected into both a 0.3% and 1% hyaluronic acid solution (prepped in $H_2O$) at a ratio of 0.7:1 DP:HA. HA was at 37° C. and the sample at room temperature. DP was added to HA via a positive displacement pipette.

After addition, an initial visual observation was made, and the samples allowed to sit for several minutes at 37° C., after which time another visual observation was made. Samples were then centrifuged for 2 minutes at 4000×g to allow for sedimentation of the precipitate. AM001 content in the supernatant was measured with SoloVPE.

After this initial content measurement, samples were vortexed briefly to fully mix the protein and HA solution, and the AM001 content measured again using SoloVPE. The visual observation results are shown in Table 4.

TABLE 4

Visual observation results

| Formulation | % HA | Appearance Post-injection (PI) | Appearance PI + 5 min 37 ° C. |
|---|---|---|---|
| AM001 in 5% Dextrose | 0.3 | Dispersed precipitate | Dispersed precipitate |
| AM001 in 5% Dextrose | 1 | Phase-separated bolus encased with precipitate | Phase-separated bolus encased with precipitate |
| AM001 in Normal Saline | 0.3 | Dispersed precipitate | Soluble |
| AM001 in Normal Saline | 1 | Phase-separated bolus; soluble at interface | Phase-separated bolus; soluble at interface |

The solubility test results are presented in Table 5.

TABLE 5

Post-Injection and Post-Agitation solubility

| Formulation | % HA, Initial | [AM001] post-inj. (mg/mL) | [AM001] post-agit. (mg/mL) | % Soluble AM001 post-agit |
|---|---|---|---|---|
| AM001 in Dextrose | 0.3 | 0.5 | 4.44 | 38.1 |
| AM001 in Dextrose | 1 | 0.31 | 1.57 | 13.5 |
| AM001 in Normal Saline | 0.3 | 14.69 | 11.62 | 98.9 |
| AM001 in Normal Saline | 1 | 12.51 | 11.51 | 97.9 |

Significant precipitation of AM001 occurs when the protein was diluted with dextrose. An increase in the % HA resulted in an increased amount of precipitated AM001. Minimal, sustained precipitation of AM001 occurred when the protein was diluted with normal saline.

This result suggests that ionic strength plays a prominent role in precipitation of AM001 when injected in HA. As a result, 5% dextrose would be the preferred diluent to maximize the amount of protein precipitated (locally) in HA upon injection. A low ionic strength AM001 formulation would be preferred for the same reason.

B. 70 and 150 mg/mL of AM011 with Arg*HCl

AM001 (formulated at 70 and 150 mg/mL protein) was injected into a 0.3% hyaluronic acid solution (prepped in $H_2O$) at a ratio of 1:1 AM001:HA via a positive displacement pipette.

After addition, samples were swirled to mix, and a visual observation noted. AM001 content in the supernatant was then measured with SoloVPE. The results are shown in Table 6.

TABLE 6

Visual Observations and Content Measurement

| HA Solution | AM001 Formulation | Mixing Ratio | Solubility Observation | pH, Post-Mixing | % Soluble Protein, Post Mixing |
|---|---|---|---|---|---|
| 0.3% in H2O | 150 mg/mL AM001 in 20 mM His (pH 5.8), 140 mM Arg*HCl, and 0.009% PS20 | 1:1 | Soluble | 5.73 | 96.3 |
| 0.3% in H2O | 150 mg/mL AM001 in 20 mM Cit (pH 4.9), 50 mM Arg*HCl, 100 mM NaCl, and 0.009% PS20 | 1:1 | Soluble | 4.93 | 100.9 |

TABLE 6-continued

Visual Observations and Content Measurement

| HA Solution | AM001 Formulation | Mixing Ratio | Solubility Observation | pH, Post-Mixing | % Soluble Protein, Post Mixing |
|---|---|---|---|---|---|
| 0.3% in H2O | 70 mg/mL AM001 in 20 mM Succ (pH 5.2), 150 mM Arg*HCl, and 0.009% PS20 | 1:1 | Soluble | 5.19 | 101.4 |
| 0.3% in H2O | 160 mg/mL AM001 in 20 mM His (pH 5.3) | 1:1 | Precipitated | 5.41 | 54.0 |

Samples formulated with Arg*HCl were soluble in 0.3% HA, even under conditions of lower relative pH (pH≤5.2). Likely this is an ionic strength effect, similar to that seen for the drug product diluted with normal saline. Concentration of the protein, however, was not a factor.

70 and 150 mg/mL AM001 were both soluble (when formulated with Arg*HCl). Without Arg*HCl, precipitation of at least half of the protein occurred when formulated in 20 mM Histidine (pH 5.3) alone. This result suggests Arg*HCl was primarily responsible for the miscibility/solubility of the protein and HA, although 20 mM Histidine may have some effect as well.

C. Temperature Effects: 5° C. vs Room Temp. Addition

The effect of protein temperature on solubility in HA (in $H_2O$) was examined. Drug Product (DP): AM001 70 mg/mL in 10 mM acetate (pH 5.2) and 260 mM sucrose.

The sample was injected into both a 0.3% and 1% hyaluronic acid solution (prepped in $H_2O$) at a ratio of 0.7:1 DP:HA. HA was at either 5° C. or 37° C., and the DP at 5° C. or room temperature.

The conditions examined were as follows: (a) 5° C. DP+5° C. HA, (b) 5° C. DP+37° C. HA, (c) Room temp. DP+37° C. HA, (d) DP+HA; storage at both 5° C. and 37° C. for 24 hrs.

After injection of Sample into HA, samples were vortexed briefly to fully mix the protein and HA solution. Samples were then centrifuged for 10+ minutes at 4000×g to allow for sedimentation of the precipitate. AM001 content in the supernatant was measured with SoloVPE (A280). Results are shown in Tables 7 and 8.

TABLE 7

Post-Injection and Post-Agitation Precipitation

| Mixture/Sample | Temp HA, Initial (° C.) | Temp DP, Initial (° C.) | [AM001] post-nj/agit (mg/mL) | % Soluble AM001 in HA |
|---|---|---|---|---|
| DP + 0.3% HA | 5 | 5 | 1.68 | 6.0 |
| DP + 1% HA | 5 | 5 | 15.3 | 54.6 |
| DP + 0.3% HA | 37 | 25 (room temp) | 1.44 | 5.1 |
| DP + 1% HA | 37 | 25 (room temp) | 13.5 | 48.2 |
| DP + 0.3% HA | 37 | 5 | 1.49 | 5.3 |
| DP + 1% HA | 37 | 5 | 12.82 | 45.8 |

The amount of soluble (i.e., non-precipitated) AM001 remaining in the HA solution after addition and mixing is listed in the las column in the above table. Comparison of the 5° C. vs. room temperature DP addition shows temperature of the DP had no impact on its solubility in HA (either at 0.3% or 1% HA).

Interestingly, the protein was more soluble in the samples with higher HA content (1%). Protein precipitation appeared to have a dependence on the ratio of protein to HA.

TABLE 8

Solubility after Storage for 24 hrs at 5° C. or 37° C.

| Sample | Temperature (° C.) | % Soluble AM001 in HA, t0 | % Soluble AM001 in HA, 24 hrs |
|---|---|---|---|
| DP + 0.3% HA | 5 | 6.0 | 3.8 |
| DP + 1% HA | 5 | 54.6 | 43.8 |
| DP + 0.3% HA | 37 | 5.1 | 5.8 |
| DP + 1% HA | 37 | 48.2 | 54.2 |

Solubility of AM001 in HA decreased when the mixture was stored at 5° C. for 24 hours. Evidenced by additional precipitate forming in the supernatant (initially clear at time-zero), as well as the concentration measurement. Solubility increased slightly at 37° C. for the 1% HA condition.

Concentration measurements made on the above mixtures indicated that temperature of the DP did not have a significant impact on its solubility in HA (either at 0.3% or 1% HA). 24-hour storage of the protein/HA solutions at 5° C. resulted in some increased precipitation of the protein.

D. Solubility of HA and Histidine Formulations

This assay examined the solubility of AM001 formulated in 20 mM Histidine (pH 5.3) when mixed with HA.

Formulated AM001 was injected into both a 0.3% and 1% hyaluronic acid solution (prepped in $H_2O$) at a ratio of 0.7:1 protein solution:HA. Formulated AM001 was added to HA via a positive displacement pipette.

The formulations examined were as follows, (a) 160 mg/mL AM001 in 20 mM Histidine (pH 5.3), (b) 70 mg/mL AM001 in 20 mM Histidine (pH 5.3), and (c) 30 mg/mL AM001 in 20 mM Histidine (pH 5.3).

After injection of DS into HA, samples were vortexed briefly to fully mix the protein and HA solution. Samples were then centrifuged for 10+ minutes at 4000×g to allow for sedimentation of the precipitate. AM001 content in the supernatant was measured with SoloVPE. The results are shown in Tables 9 and 10.

TABLE 9

Post-Injection and Post-Agitation Precipitation

| [Protein], Initial (mg/mL) | % HA, Initial | Protein/HA (w/w) | [AM001] post-inj/agit (mg/mL) | % Soluble AM001 in HA |
|---|---|---|---|---|
| 159 | 0.3 | 53 | 20.43 | 31.2 |
| 159 | 1 | 16 | 21.6 | 33.0 |
| 70 | 0.3 | 23 | 1.99 | 6.9 |
| 70 | 1 | 7 | 23.36 | 80.7 |
| 30 | 0.3 | 10 | 6.59 | 53.5 |
| 30 | 1 | 3 | 12.44 | 101.1 |

The amount of soluble (i.e., non-precipitated) AM001 remaining in the HA solution after addition and mixing is listed in the last column in the above table. Based on the above data set, the ratio of protein to HA dictates solubility of AM001 under these specific conditions.

Consistent with data obtained using drug product; same experimental conditions 70 mg/mL AM001 in 0.3% HA (3 mg/mL) resulted in the largest amount of insoluble/precipitated protein. Here the ratio of protein to HA was 23:1 on a weight basis.

TABLE 10

Comparison of Histidine Forms and Drug Product

| [Protein], Initial (mg/mL) | % HA, Initial | % Soluble, AM001 in His (mg/mL) | % Soluble, DP (mg/mL) |
|---|---|---|---|
| 70 | 0.3 | 6.9 | 5.1 |
| 70 | 1 | 80.7 | 48.2 |
| 30 | 0.3 | 53.5 | 48.5 |
| 30 | 1 | 101.1 | 92.8 |

The amount of soluble (i.e., non-precipitated) AM001 remaining in the HA solution after addition and mixing is listed in the above table for both AM001 formulated in 20 mM Histidine (pH 5.3) and drug product (DP). In general, the Histidine forms are more soluble than drug product in HA.

The ratio of protein to HA appears to play a significant role in the solubility of AM001 in HA solutions. 70 mg/mL AM001 mixed with 0.3% HA (3 mg/mL) resulted in the largest amount of insoluble/precipitated protein (~93% precipitated). The Histidine forms tend to be slightly more soluble in HA E. IVR Study For this study, injected 0.5 mL of the following AM001 formulations at the bottom of sterile, conical tubes: (a) 150 mg/mL AM001 in 20 mM His (pH 5.8), 150 mM Arg*HCl, and 0.009% PS20, (b) Drug product (70 mg/mL AM001), (c) 30 mg/mL drug product diluted in 5% dextrose, and (d) 30 mg/mL drug product diluted in normal saline.

The protein was phase separated from the HA (based on density) at the bottom of the tube. 2 mL of HA solution made up the remaining volume in the tube (HA soln.=0.3% HA in PBS (pH 7.4)). IVR was conducted at 37° C. with no mixing (i.e., static).

1.5 mL of HA solution was harvested in 24 hour intervals. 1.5 mL of additional HA solution (at 37° C.) was added to replace the harvested HA volume. Study time was 6 days.

The harvested solution was measured for protein content using SoloVPE (A280). The results are shown in Table 11.

TABLE 11

Protein Remaining after 6 Days

| Formulation | Protein Remaining, Day 6 (mg/mL) | % Protein Remaining vs. Time-Zero |
|---|---|---|
| 150 mg/mL in His/Arg (pH 5.8) | 94.8 | 62.4 |
| DP (70 mg/mL) | 39.4 | 58.0 |
| 30 mg/mL DP in DW | 16.1 | 56.5 |
| 31 mg/mL DP in NS | 14.7 | 51.2 |

The results show that release rates increased with increasing protein concentration. Having a higher concentration of protein appears to be of benefit, based on the total amount of protein remaining after 6 days.

Example 5. Comparison of AM001, EMAC, and Rat IgG1 Solubility in Different Concentrations of Hyaluronic Acid This example measured solubility of AM001, EMAC (Emactuzumab) and an $IgG_1$ (from rat) as a function of concentrations of hyaluronate (HA).

0.3% and 1% HA were prepared in milliQ water; 0.3% HA were prepared in PBS (pH 7.4). The proteins/formulations examined were as follows: (a) 30 mg/mL AM001 in 10 mM acetate (pH 5.2), 9% sucrose, and 0.002% PS20, (b) 30 mg/mL EMAC in 20 mM His (pH 6.0), 240 mM trehalose, and 0.02% PS20, and (c) 22 mg/mL $IgG_1$ (from rat) in 10 mM acetate (pH 5.2) and 9% sucrose.

The protein was mixed at a ratio of 1:1 protein:HA (room temperature protein solutions and 37° C. HA solutions). After injection of protein into HA, the samples were vortexed briefly to fully mix the protein and HA solution. Samples were then centrifuged for 20+ minutes at 4000×g to allow for sedimentation of the precipitate. Protein content in the supernatant was measured with SoloVPE (concentration from A280). The results are shown in Tables 12 and 13.

TABLE 12

Solubility Results for HA Prepped in Water

| Protein Sample | % HA | [Protein] (mg/mL), post-mixing | % Soluble Protein, post-mixing |
|---|---|---|---|
| AM001 | 0.3 | 2.95 | 20.2 |
| AM001 | 1 | 11.49 | 78.6 |
| EMAC | 0.3 | 2.62 | 17.5 |
| EMAC | 1 | 8.71 | 58.1 |
| IgG1, Rat | 0.3 | 0.78 | 7.1 |
| IgG1, Rat | 1 | 5.55 | 50.5 |

The amount of soluble (i.e., non-precipitated) protein remaining in the HA solutions after addition and mixing is listed in the last column in the above table. AM001 and EMAC had similar solubility in 0.3% HA. Solubility increased for all 3 proteins in 1% HA.

In general, these findings suggest that solubility will be similar for most IgGs if they are formulated at low ionic strength and at a pH sufficiently below their pI to be positively charged. Precipitation is contemplated to be due to ion-pairing of the positively charged IgG with HA.

TABLE 13

Solubility Results for HA Prepped in PBS (pH 7.4)

| Protein Sample | % HA | [Protein] (mg/mL), post-mixing | % Soluble Protein, post-mixing |
|---|---|---|---|
| AM001 | 0.3 | 14.54 | 99.6 |
| EMAC | 0.3 | 14.98 | 99.9 |
| IgG1, Rat | 0.3 | 10.87 | 98.8 |

All three proteins initially precipitated to some degree (locally) when injected into HA. This is likely due to regions of low ionic strength in the non-mixed solution, which facilitates formation of the insoluble IgG/HA ion-pair. However, all three proteins are 100% soluble when the solution is mixed. This is contemplated to be the result of sufficient ionic strength to dissociate the IgG/HA ion-pair.

Example 6. Comparison of AM001 and EMAC Solubility in Hyaluronate as a Function of Protein Concentration This example measured solubility of AM001 and EMAC (Emactuzumab) as a function of protein concentration in a solution of 0.3% hyaluronate (HA).

0.3% HA was prepared in milliQ water. The base formulations were as follows: AM001 in 10 mM acetate (pH 5.2), 9% sucrose, and 0.002% PS20; EMAC in 20 mM His (pH 6.0), 240 mM trehalose, and 0.02% PS20. The samples were prepared at the following concentrations in the above formulations: 1, 5, 10, 15, 20, and 30 mg/mL AM001 or EMAC.

Each protein was mixed at a ratio of 1:1 protein:HA at room temperature. After addition of protein into HA, samples were vortexed briefly to fully mix the protein and HA solution. The samples were then centrifuged to allow for sedimentation of the precipitate. Protein content in the supernatant was measured with SoloVPE (concentration from A280).

The observed results are shown in Table 14. The amount of soluble (i.e., non-precipitated) protein remaining in the HA solution after addition and mixing is listed in the last column in Table 14.

TABLE 14

Solubility of antibody in each solution

| Protein | [Protein] (mg/mL), initial | [Protein] (mg/mL), post-mixing | % Soluble Protein post-mixing |
| --- | --- | --- | --- |
| EMAC | 1.05 | 0.52 | 99.0 |
| EMAC | 4.86 | 2.24 | 92.2 |
| EMAC | 9.81 | 3.16 | 64.3 |
| EMAC | 14.95 | 3.34 | 44.7 |
| EMAC | 22.58 | 3.22 | 28.5 |
| EMAC | 30.1 | 2.68 | 17.8 |
| AM001 | 1.01 | 0.49 | 97.0 |
| AM001 | 4.99 | 1.99 | 79.8 |
| AM001 | 9.87 | 2.92 | 59.2 |
| AM001 | 15.07 | 2.74 | 36.4 |
| AM001 | 20.35 | 2.36 | 23.2 |
| AM001 | 28.86 | 2.11 | 14.6 |

Increasing amounts of precipitation occurred as the protein to hyaluronate ratio increased. This explains the increased solubility of these IgGs in 1% hyaluronate versus 0.3% hyaluronate. The solubility trends for EMAC and AM001 were similar in this study.

Example 7. Comparison of AM001 and EMAC Solubility in Hyaluronate as a Function of Formulation pH This example measured solubility of AM001 and EMAC (Emactuzumab) as a function of pH in the presence of 0.3% hyaluronate (HA).

The base protein formulations examined were as follows: (a) 30 mg/mL AM001 in 10 mM acetate (pH 5.2), 9% sucrose, and 0.002% PS20, and (b) 30 mg/mL EMAC in 20 mM His (pH 6.0), 240 mM trehalose, and 0.02% PS20.

These formulations were titrated up and down to targeted values of pH by addition of small amounts of acid or base. Proteins were mixed at a ratio of 1:1 protein:HA at room temperature. After addition of protein into HA, samples were vortexed briefly to fully mix the protein and HA solution. Samples were then centrifuged to allow for sedimentation of the precipitate. Protein content in the supernatant was measured with SoloVPE (concentration from A280). The results are shown in Table 15.

TABLE 15

Solubility Results

| Protein | pH | [Protein] (mg/mL), post-mixing | % Soluble Protein post-mixing |
| --- | --- | --- | --- |
| EMAC | 4.48 | 1.26 | 8.5 |
| EMAC | 6.29 | 3.34 | 22.5 |
| EMAC | 7.46 | 15.26 | 102.6 |
| EMAC | 7.91 | 15.14 | 101.8 |
| AM001 | 4.55 | 0.10 | 0.7 |
| AM001 | 5.15 | 2.36 | 16.4 |
| AM001 | 6.32 | 14.48 | 100.3 |
| AM001 | 7.41 | 14.34 | 99.4 |

The results suggest that pH plays a role in the ability of the IgG to interact and form a precipitate with hyaluronate. It is contemplated that precipitation is due to ion-pairing of the positively charged IgG with HA. As result, as the pH approaches that of the pI (and above), the ability of the IgG to ion-pair with the hyaluronate will diminish.

Example 8. Solubility of EMAC in Hyaluronate as a Function of Formulation pH (pH 6-7)

This example measured solubility of EMAC as a function of formulation pH (pH 6-7) in a solution of 0.3% hyaluronate (HA).

The EMAC base formulation utilized for this study was as 30 mg/mL EMAC in 20 mM His (pH 6.3), 240 mM trehalose, and 0.02% PS20.

The base formulation was titrated up or down to targeted values of pH by addition of small amounts of acid or base. EMAC was mixed at a ratio of 1:1 protein:HA at room temperature. After addition of protein into HA, samples were vortexed briefly to fully mix the protein and HA solution. Samples were then centrifuged to allow for sedimentation of the precipitate. Protein content in the supernatant was measured with SoloVPE (concentration from A280). The results are presented in Table 16.

TABLE 16

EMAC Solubility Results

| Protein | pH | [Protein] (mg/mL), post-mixing | % Soluble Protein post-mixing |
| --- | --- | --- | --- |
| EMAC | 6.93 | 7.98 | 53.2 |
| EMAC | 6.69 | 5.53 | 36.8 |
| EMAC | 6.36 | 3.82 | 25.4 |
| EMAC | 5.98 | 1.55 | 10.4 |

Increasing amounts of precipitation occurred as the pH of the EMAC formulation was decreased from pH 7 to pH 6. This result suggests that the increasing positive charge on EMAC as a function of decreasing pH results in increased interaction with the hyaluronate.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the

The invention claimed is:

1. A method for providing extended release of an antibody in a mammalian subject in need thereof, comprising injection of an aqueous solution comprising at least 15 mg/mL of the antibody to or near a tissue in the mammalian subject,
   wherein the antibody is AM001, and the solution has a pH between 4.5 and 5.5,
   wherein AM001 comprises a heavy chain comprising the amino acid sequence of SEQ ID NO:7 and a light chain comprising the amino acid sequence of SEQ ID NO:8,
   wherein the aqueous solution includes less than 100 mM of an alkaline salt or a salt of an amino acid,
   wherein the tissue contains hyaluronic acid (HA),
   wherein the antibody reversibly forms gel with HA.

2. A method for providing extended release of an antibody in a mammalian subject in need thereof, comprising injection of an aqueous solution comprising at least 15 mg/mL of the antibody to or near a tissue in the mammalian subject,
   wherein the antibody is Emactuzumab, and the solution has a pH between 5.5 and 6.5,
   wherein the aqueous solution includes less than 100 mM of an alkaline salt or a salt of an amino acid,
   wherein the tissue contains hyaluronic acid (HA),
   wherein the antibody reversibly forms gel with HA.

3. The method of claim 1, wherein the tissue is a joint.

4. The method of claim 1, wherein the solution further comprises HA.

5. The method of claim 2, wherein the tissue is a joint.

* * * * *